United States Patent
Peters et al.

(10) Patent No.: US 11,266,646 B2
(45) Date of Patent: Mar. 8, 2022

(54) USE OF CHYMASE INHIBITORS FOR THE TREATMENT OF ENDOMETRIOSIS, POST OPERATIVE FIBROSIS AND DISEASES WHICH ARE CHARACTERIZED BY FIBROSIS FORMATION

(71) Applicant: BAYER PHARMA AKTIENGESELLSCHAFT, Berlin (DE)

(72) Inventors: Michaele Peters, Berlin (DE); Markus Koch, Berlin (DE); Thomas Zollner, Berlin (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 98 days.

(21) Appl. No.: 16/471,928

(22) PCT Filed: Dec. 13, 2017

(86) PCT No.: PCT/EP2017/082569
§ 371 (c)(1),
(2) Date: Jun. 20, 2019

(87) PCT Pub. No.: WO2018/114514
PCT Pub. Date: Jun. 28, 2018

(65) Prior Publication Data
US 2019/0381040 A1 Dec. 19, 2019

(30) Foreign Application Priority Data
Dec. 20, 2016 (EP) .................................. 16205339

(51) Int. Cl.
*A61K 31/506* (2006.01)
*A61P 41/00* (2006.01)
*A61K 31/536* (2006.01)

(52) U.S. Cl.
CPC .......... *A61K 31/506* (2013.01); *A61K 31/536* (2013.01); *A61P 41/00* (2018.01)

(58) Field of Classification Search
None
See application file for complete search history.

(56) References Cited

U.S. PATENT DOCUMENTS

| | | | |
|---|---|---|---|
| 7,071,220 B2 * | 7/2006 | Satoh | C07D 333/62 514/365 |
| 9,695,131 B2 | 7/2017 | Furstner et al. | |
| 9,751,843 B2 | 9/2017 | Furstner et al. | |
| 9,926,305 B2 | 3/2018 | Olenik et al. | |
| 2004/0018984 A1 | 1/2004 | Miyazaki | |
| 2010/0029637 A1 | 2/2010 | De Lombaert et al. | |
| 2015/0148340 A1 | 5/2015 | Füstner et al. | |
| 2016/0287599 A1 | 10/2016 | Furstner et al. | |
| 2017/0267648 A1 | 9/2017 | Furstner et al. | |

FOREIGN PATENT DOCUMENTS

| | | | |
|---|---|---|---|
| WO | 2013/167495 | 11/2013 | |
| WO | WO-2013167495 A1 * | 11/2013 | ............ A61P 11/06 |

OTHER PUBLICATIONS

Okamoto et al. "Chymase inhibitors may prevent postoperative adhesion formation," Fertility and Sterility vol. 77, No. 5, May 2002 (Year: 2002).*
WO-2013167495-A1—English Translation (Year: 2021).*
Miyazaki et al., "Pathological Roles of Angiotensin II Produced by Mast Cell Chymase and the Effects of Chymase Inhibition in Animal Modes," Pharmacology and Therapeutics, Dec. 2006, 112(3), pp. 668-676.
Shiota et al., "A Role for Cardiac Mast Cells in the Pathogenesis of Hypertensive Heart Disease," Journal of Hypertension, 2003, 21(10), pp. 1935-1944.
Zanini et al., "Chymase-Positive Mast Cells Play a Role in the Vascular Component of Airway Remodeling in Asthma," J. Allergy Clin. Immunol., Aug. 2007, 120(2), pp. 329-333.
Heuston et al., "Chymase Inhibition as a Pharmacological Target: A Role in Inflammatory and Functional Gastrointestinal Disorders?," British Journal of Pharmacology, May 2012, 167, pp. 732-740.
Hart, "Curbing Inflammation in Multiple Sclerosis and Endometriosis: Should Mast Cells be Targeted?," International Journal of Inflammation, Sep. 2015, vol. 2015, 10 pages.
Pejler et al., "Mast Cell Proteases," Advances in Immunology., 2007, 95, pp. 167-255.
Lopez-Castejon et al., "Understanding the Mechanism of IL-1β Secretion," Cytokine & Growth Factor Reviews, Oct. 2011, 22, pp. 189-195.
Okamoto et al., "Chymase Inhibitor, BCEAB, Suppressed Peritoneal Adhesion Formation in Hamster," Journal of Surgical Research, Aug. 2002, 107, pp. 219-222.
Okamoto et al., "Chymase Inhibitors may Prevent Postoperative Adhesion Formation," Fertility and Sterility, May 2002, 77(5), pp. 1044-1048.
Greco et al., "Discovery of Potent, Selective, Orally Active, Nonpeptide Inhibitors of Human Mast Cell Chymase," J. Med. Chem., Jan. 2007, 50, pp. 1727-1730.
Maryanoff et al., "Dual Inhibition of Cathespin G and Chymase is Effective in Animal Models of Pulmonary Inflammation," Am J. Respir Crit Care Med., 2010, 181, pp. 247-253.
Garavilla et al., "A Novel, Potent Dual Inhibitor of the Leukocyte Proteases Cathespin G and Chymase," The Journal of Biological Chemistry, May 2005, 280(18), pages 18001-18007.
Lousse et al., "Peritoneal Endometriosis is an Inflammatory Disease," Frontiers in Bioscience, Jan. 2012, 4, pp. 23-40.

(Continued)

*Primary Examiner* — Jeffrey S Lundgren
*Assistant Examiner* — Michael J Schmitt
(74) *Attorney, Agent, or Firm* — Quarles & Brady LLP

(57) ABSTRACT

The present application relates to the use of bicyclic-substituted uracil derivatives, alone or in combinations with other active ingredients for the treatment and/or prophylaxis of diseases, in particular for the treatment and/or prophylaxis of inflammatory and fibrotic disorders, for the treatment of endometriosis, of endometriosis-associated fibrosis, of adenomyosis and of pain associated with an endometriosis disorder and also of postoperative peritoneal fibrosis and adhesion formation.

5 Claims, 1 Drawing Sheet

(56) References Cited

OTHER PUBLICATIONS

McKinnon et al, "Inflammation and Nerve Fiber Interaction in Endometriotic Pain," Trends in Endocrinology and Metabolism, Jan. 2015, 26(1), 10 pages.

Laux-Biehlmann et al., "Menstruation Pulls the Trigger for Inflammation and Pain in Endometriosis," Trends in Pharmacological Sciences, May 2015, 36(5), pp. 270-276.

Sugamata et al., "Increase of Activated Mast Cells in Human Endometriosis," American Journal of Reproductive Immunology, Jan. 2005, 53, pp. 120-125.

Fujiwara et al., "Localization of Mast Cells in Endometrial Cysts," American Journal of Reproductive Immunology, Jan. 2004, 51, pp. 341-344.

Anaf et al., "Pain, Mast Cells, and Nerves in Peritoneal, Ovarian, and Deep Infiltrating Endometriosis," Fertility and Sterility, Mar. 2006, 86(5), pp. 1336-1343.

Xu et al., "Role of Mast Cells and Myofibroblasts in Human Peritoneal Adhesion Formation," Annals of Surgery, Nov. 2002, 236(5), pp. 593-601.

Kirchhoff et al., "Mast Cells in Endometriosis: Guilty or Innocent Bystanders?," Expert Opinion on Therapeutic Targets, Feb. 2012, 16(3), pp. 237-241.

Paula et al., "The Intricate Role of Mast Cell Proteases and the Annexin A1-FPR1 System in Abdominal Wall Endometriosis," J. Mol. Hist., 2015, 46, pp. 33-43.

"CME Questions for Jun. 2003 Issue of the Journal of Urology," Journal of Urology, Lippincott Williams, and Wilkins, Jun. 2003, 169(6), 1 page.

Binda et al., "Targeting Mast Cells: A New Way to Treat Endometriosis," Expert Opinion on Therapeutic Targets, 2017, 21(1), pp. 67-75.

Okamoto et al., "Significance of Chymase Inhibition for Prevention of Adhesion Formation," European Journal of Pharmacology, 2004, 484, pp. 357-359.

\* cited by examiner

Reduction of adhesion formation caused by endometriosis by treatment with example compound 189 of WO 2013/167495.
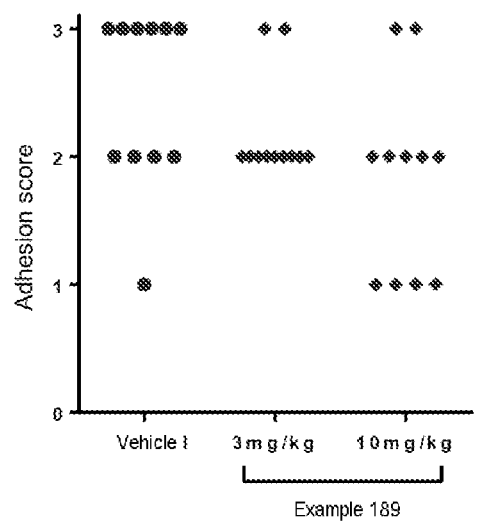

USE OF CHYMASE INHIBITORS FOR THE TREATMENT OF ENDOMETRIOSIS, POST OPERATIVE FIBROSIS AND DISEASES WHICH ARE CHARACTERIZED BY FIBROSIS FORMATION

CROSS REFERENCE TO RELATED APPLICATIONS

This application is the U.S. national stage entry under 35 U.S.C. 371 of PCT/EP2017/082569 filed Dec. 13, 2017, which is hereby incorporated by reference herein, which claims benefit of priority to European Patent App. No. 16205339.1 filed on Dec. 20, 2016.

The present applications relates to the use of bicyclic-substituted uracil derivatives, alone or in combinations with other active ingredients for the treatment and/or prophylaxis of diseases, in particular for the treatment and/or prophylaxis of inflammatory and fibrotic disorders, for the treatment of endometriosis, of endometriosis-associated fibrosis, of adenomyosis and of pain associated with an endometriosis disorder and also of postoperative peritoneal fibrosis and adhesion formation.

In many disorders, local inflammation leads to fibrosis. Fibrosis refers to a pathological proliferation of the connective tissue, in human and animal tissues and organs, the main constituent of which are collagen fibres. When referring to two different tissues or organs, fibroses attach to one another leading to adhesions which may limit the function of the organs. Particularly in the case of therapy and/or prophylaxis of such disorders with local inflammation and fibrosis, the chymase inhibitors described here are suitable since they prevent a critical pathomechanism of mast cells.

Mast cells are key cells in the induction and regulation of inflammatory processes. All mast cells are independent of species and have common localization characteristic features:
  they express the membrane-bound receptors FcεRI (for IgE) and kit (for stem cell factor, SCF).
  they produce metachromatic cytoplasmic granules comprising preformed mediators such as histamine, proteases and proteoglycans.

Human mast cells can be divided into tryptase-positive and/or chymase-positive populations.

Activated mast cells play an important role in wound healing and in inflammatory processes, for example, fibroses in wounds, angiogenesis and cardiac remodelling (Miyazaki et al., Pharmacol. Ther. 112 (2006), 668-676; Shiota et al., J. Hypertens. 21 (2003), 1823-1825). Chymase-positive mast cells can also play an important role in the vascular remodelling of the respiratory pathways in the event of asthma. An increased number of mast cells has been found in endobronchial biopsies of asthma patients (Zanini et al., J. Allergy Clin. Immunol. 120 (2007), 329-333).

In addition to a function in the case of asthma and cardiovascular disorders, activated, chymase-positive mast cells are attributed important pathophysiological functions in other inflammatory disorders (Heuston et al., Br. J. Pharmacol. 167 (2012) 732-740), an example is endometriosis (Hart, Int J Inflam. 26 (2015) 1-10).

The pathomechanism of chymase-positive mast cells in such disorders is due to the release of active chymase. After activation of the mast cells, chymase is released into the extracellular matrix and activated. Chymase is a chymotrypsin-like serine protease which is stored as a macromolecular complex with heparin proteoglycans in secretory vesicles of mast cells. As a protease, chymase cleaves a series of substrates. Chymase is involved in various physiological processes (activation of pro-inflammatory cytokines, recruitment of immune cells, fibrosis and adhesion formation (Pejler et al. 95. 2007, Adv Immunol. 167-255). These processes all have a pathological significance, also in endometriosis and postoperative fibrosis.

Chymase leads to degradation of extracellular matrix proteins, such as fibronectin, procollagen and vitronectin, and to the breakoff of focal adhesions. It effects the activation and release of TGFß (transforming growth factor beta) from its latent form, which plays an important role in the formation of peritoneal adhesions and fibrosis after operations and also in endometriosis. The action of chymase leads to release and activation of the cytokine interleukin 1 beta (IL-1β), which is a main mediator of pro-inflammatory reactions (Lopez-Castejon et al., Cytokine Growth Factor Rev. 22 (2011) 189-95). Activation of interleukin 1 beta leads to sensitization of nerve cells and thus development of the sensation of pain. Other pro-inflammatory cytokines are also activated by the action of chymase. This leads to recruitment of further immune cells which increase inflammation locally in the tissues. Chymase is therefore involved in enhancement of inflammation, the development of pain, the recruitment of immune cells and the formation of adhesions. Chymase has been described as a possible pharmacological target for the treatment of inflammatory disorders (Heuston et al., Br. J. Pharmacol. 167 (2012) 732-740).

The possibility of using chymase inhibitors for the treatment of different diseases has been demonstrated in numerous studies involving animal experimentation. For instance, the formation of peritoneal adhesions could be reduced by inhibition of chymase in a hamster model (Okamoto et al, J. Surg. Res., 107 (2002) 219-222 and Fertil and Steril. 77(2002) 1044-1048). It could also be shown in paw oedema models that inflammations are reduced by inhibition of chymase (Greco et al., J Med Chem 50 (2007) 1727-1730; Maryanoff et al, Am J Respir Crit Care Med 181 (2010) 247-253). Beta-ketophosphonate, a chymase inhibitor, blocks the generation of IL-1β and prevents the migration of inflammatory cells in a peritonitis model (Garavilla et al., J Biol Chem 280 (2005) 18001-7).

Endometriosis is an inflammatory disorder (Lousse J C et al., Front Biosci. 4 (2012) 23-40), which is characterized by the growth of endometrial tissue (lesions) outside the Cavum uteri in the abdominal cavity and the occurrence of peripheral nerve endings in the vicinity of lesions (McKinnon et al., Trends Endocrinol & Metab. 26 (2015) 1-10). Characteristic of endometriosis is the formation of an inflammatory environment in the abdominal cavity which is often associated with fibrosis and the formation of adhesions caused thereby. The main symptoms of this disorder are pain.

Inflammation is considered as a potential important pathomechanism of endometriosis and as a cause of the pain associated with endometriosis (Laux-Biehlmann et al., Trends in Pharmacol Sci. 36 (2015) 270-276).

Endometriosis is treated as standard practice by hormone and/or pain therapy. The operative removal of the endometriotic lesions and fibroses is available as non-medicament-related therapy.

Hormonal therapy effects a lowering of the oestrogen level, which is considered as an essential factor in the development and maintenance of endometriosis. The most important active ingredients in the hormonal therapy of endometriosis are:
  gestagens such as medroxyprogesterone acetate, levonorgestrel, dydrogesterone and dienogest. Administration can be both oral (for example dienogest in Visanne®) and local (for example levonorgestrel in an intrauterine system).

monophasic oestrogen-gestagen combination preparations, which are present, for example, in oral contraceptives (pills), which result in reformation of the endometrium and pain reduction when administered continuously.

gonadotropin-releasing hormone (GnRH) analogues which block the hypothalamus-hypophysis axis and lower the oestrogen level to within a range which is normally to be expected in post-menopausal women. These are complaints such as hot flushes, sleep disturbances, vaginal dryness, osteoporosis and mood swings.

Hormonal contraceptives (pills) and intrauterine levonorgestrel-releasing systems (intrauterine pessaries) are not approved for the treatment of endometriosis in Germany. Their therapeutic use is outside of the approved range of indications ("off label").

All hormonal therapies described, on discontinuation, lead to a re-occurrence of symptoms and therefore ought to be implemented over a very long time period which is not possible in all cases. For instance, hormonal therapies such as, for example, GnRH analogues, produce a temporary condition as in the menopause with the corresponding attendant symptoms. For instance, the female patients suffer hot flushes, sleep disturbances, mood swings, loss of libido and osteoporosis which renders a therapy duration of more than 6 months difficult.

Long-term therapy with gestagens or the pill leads in many women to side-effects such as headaches and physical changes due to the influence of the endogenous hormonal cycle. In addition, many female patients are resistant to hormonal therapy with the pill or gestagens.

To treat pain, analgesics such as acetylsalicylic acid, ibuprofen or diclofenac may be administered. Pain therapy can only be used for short periods and in close consultation with the doctor due to side-effects on the kidneys and the stomach and also the cardiovascular system.

In the case of operative therapy, for example with electrical current, laser or scalpel, it is attempted to remove the endometrial foci as completely as possible. The intervention is carried out predominantly in the context of an abdominal laporoscopy, an abdominal incision sometimes being necessary. In pronounced cases, even a part of the ovaries or fallopian tubes sometimes have to be removed. After operative removal of endometriosis, re-occurence of the disorder in the longer term often results.

The need for novel therapies for the treatment of endometriosis which may be used chronically and which are free from the side-effects mentioned above is therefore immense.

Even in the case of endometriosis, mast cells and in particular chymase from mast cells are involved in the pathophysiology: comparison of endometriotic lesions with the endometrium shows a significantly elevated number of activated mast cells in endometriotic lesions (Sugamata et al., J. Reprod. Immunol. 53 (2005) 120-125); Fujiwara et al, J. of Reprod. Immunol. 51 (2004) 341-344). A significant increase in the number of activated and chymase-expressing mast cells in the proximity of peritoneal nerves and in deeply infiltrated lesions in endometriosis has been described (Anaf et al., Fertil. Steril. 86 (2006) 1336-1343). An increase in mast cells has also been shown in peritoneal adhesions (Xu et al., Ann. Surg. 236 (2001) 593-601).

Mast cells are attributed an important pathophysiological role in endometriosis (Kirchhoff et al., Expert Opin Ther Targets, 16 (2012) 237-241; Hart, Int J Inflam. 26 (2015) 1-10).

Mast cells in endometriotic lesions are chymase-positive (Anaf et al., Fertil. Steril. 86, 2006, 1336-1343). In this case, mast cell-specific chymase expression in endometriotic lesions is significantly elevated in comparison to mast cell-specific expression of chymase in the endometrium (Paula et al., J Mol Histol. 46 (2015) 33-43).

Postoperative peritoneal fibrosis and adhesions are triggered by peritoneal operations, for example laparoscopies or laparotamies. These operations frequently lead to injuries to the tissue of organs and local inflammation foci resulting therefrom. These local inflammations in the peritoneum lead to fibrosis and the connection of organs by fibrotic tissue, i.e. adhesions. Adhesions of organs in the abdomen can impair the function of the organs and may thus lead, inter alia, to subfertility, to intestinal blockage and to chronic abdominal pain.

For preventing such side-effects of peritoneal operations, physical barriers are currently used during the operation to reduce the formation of adhesions. However, this is only possible directly during the operation and therefore the effect is only short term. For long-term prevention of postoperative fibroses and adhesions, medicaments such as corticosteroids or other strong immonosuppresives may be used which inhibit the immune system and activity of the connective tissue cells. The use of these medicaments however is associated with severe side-effects such as so-called Cushing's syndrome, an increase in blood pressure, an increase in blood sugar and an increased occurrence of infection.

The need for novel therapies for the prevention of postoperative fibroses and adhesions which may be used chronically and which are free from the side-effects mentioned above is therefore immense.

Here, the chymase formed by mast cells is also of particular importance for the pathophysiology. For instance, the formation of peritoneal adhesions could be reduced by inhibition of chymase in a hamster model (Okamoto et al, J. Surg. Res., 107 (2002) 219-222 and Fertil and Steril. 77(2002) 1044-1048).

The object of the present invention is to provide possibilities for the treatment and prevention of inflammatory disorders and chronic pain disorders of the pelvic cavity, such as endometriosis and/or secondary dysmenorrhoea and/or postoperative fibrosis and adhesions. In contrast to the methods known from the prior art, the novel treatment possibilities are characterized in that they can be used in a chronic treatment without thereby influencing the hormonal cycle of the woman or the occurrence of infection. In particular, possibilities should be found for the treatment and prevention of endometriosis, of endometriosis-associated fibrosis, of adenomyosis, of pain associated with an endometriosis disorder and the treatment and prevention of postoperative fibroses and adhesions.

The present invention relates to the use of compounds of the general formula (I)

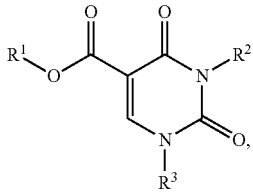

in which
R¹ is hydrogen or $(C_1-C_4)$-alkyl,
R² is a group of the formula

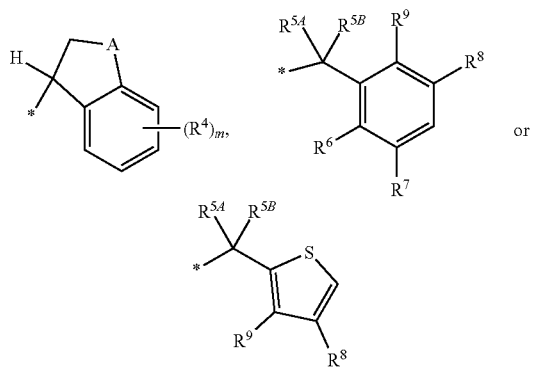

where
* is the point of attachment to the uracil nitrogen atom,
A is —CH₂—, —CH₂—CH₂—, —O—CH₂-## or oxygen,
in which
## is the point of attachment to the phenyl ring,
m is a number 0, 1 or 2,
R⁴ is halogen, difluoromethyl, trifluoromethyl, $(C_1-C_4)$-alkyl, difluoromethoxy, trifluoromethoxy or $(C_1-C_4)$-alkoxy,
$R^{5A}$ is hydrogen or deuterium,
$R^{5B}$ is hydrogen, deuterium or $(C_1-C_4)$-alkyl,
R⁶ is hydrogen or fluorine,
R⁷ is hydrogen or fluorine,
R⁸ is halogen, difluoromethyl, trifluoromethyl, $(C_1-C_4)$-alkyl or nitro,
R⁹ is hydrogen, halogen, difluoromethyl, trifluoromethyl, $(C_1-C_4)$-alkyl, nitro or $(C_1-C_4)$-alkylthio,
R³ is a group of the formula

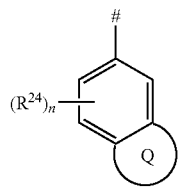

where
# is the point of attachment to the uracil nitrogen atom,
the ring Q is 5- to 7-membered heterocyclyl or 5- or 6-membered heteroaryl, in which 5- to 7-membered heterocyclyl and 5- or 6-membered heteroaryl may be substituted by 1 to 4 substituents independently selected from the group of halogen, difluoromethyl, trifluoromethyl, trideuteromethyl, $(C_1-C_6)$-alkyl, $(C_3-C_7)$-cycloalkyl, oxo, hydroxyl, $(C_1-C_4)$-alkylcarbonyl, $(C_1-C_4)$-alkoxycarbonyl, aminocarbonyl and $(C_1-C_4)$-alkylsulfonyl,
in which $(C_1-C_6)$-alkyl and $(C_3-C_7)$-cycloalkyl may in turn be substituted by 1 to 3 substituents independently selected from the group of halogen, cyano, trifluoromethyl, $(C_3-C_7)$-cycloalkyl, hydroxyl, $(C_1-C_4)$-alkoxy and 4- to 7-membered heterocyclyl,
and
in which two $(C_1-C_6)$-alkyl radicals bonded to a carbon atom of 5- to 7-membered heterocyclyl and 5- or 6-membered heteroaryl, together with the carbon atom to which they are bonded, may form a 3- to 6-membered carbocycle,
$R^{24}$ is halogen, $(C_1-C_4)$-alkyl or $(C_1-C_4)$-alkoxy,
n is a number 0, 1, 2 or 3,
and salts, solvates and solvates of the salts thereof for the treatment and prevention of endometriosis, of endometriosis-associated fibrosis, of adenomyosis, of pain associated with an endometriosis disorder and the treatment and prevention of postoperative fibroses and adhesions.

In a further embodiment of the invention, the compounds are suitable for use in the treatment of endometriosis, of endometriosis-associated fibrosis, of adenomyosis and of pain associated with an endometriosis disorder, of endometriosis-associated adhesions and fibroses, of endometriosis-associated symptoms such as dysmenorrhoea, dyspareunia, dysuria or dyschezia and also of endometriosis-associated subfertility.

In a further embodiment of the invention, the compounds are suitable for use in the treatment and prevention of postoperative adhesions in the abdominal cavity and to prevent subfertility caused by adhesions.

In a further embodiment of the invention, the compounds are suitable for the treatment of Dupuytren's contracture (a disorder of the connective tissue of the palms) and in the treatment and/or prophylaxis of chronic pain in the pelvic cavity.

In the context of the present invention, unless specified otherwise, the substituents are defined as follows:

Alkyl in the context of the invention is a straight-chain or branched alkyl radical having the particular number of carbon atoms specified. Preferred examples include: methyl, ethyl, n-propyl, isopropyl, n-butyl, isobutyl, 1-methylpropyl, tert-butyl, n-pentyl, isopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl, 2-ethylbutyl, 1,4-dimethylpentyl, 4,4-dimethylpentyl and 1,4,4-trimethylpentyl.

Cycloalkyl in the context of the invention is a monocyclic saturated alkyl radical having 3 to 7 carbon atoms. Preferred examples include: cyclopropyl, cyclobutyl, cyclopentyl, cyclohexyl and cycloheptyl.

Alkylcarbonyl in the context of the invention is a straight-chain or branched alkyl radical having 1 to 4 carbon atoms and a carbonyl group attached in the 1 position. Preferred examples include: methylcarbonyl, ethylcarbonyl, n-propylcarbonyl, isopropylcarbonyl, n-butylcarbonyl, isobutylcarbonyl and tert-butylcarbonyl.

Alkoxy in the context of the invention is a straight-chain or branched alkoxy radical having 1 to 4 carbon atoms.

Preferred examples include: methoxy, ethoxy, n-propoxy, isopropoxy, n-butoxy and tert-butoxy.

Alkoxycarbonyl in the context of the invention is a straight-chain or branched alkoxy radical having 1 to 4 carbon atoms and a carbonyl group attached to the oxygen. Preferred examples include: methoxycarbonyl, ethoxycarbonyl, n-propoxycarbonyl, isopropoxycarbonyl and tert-butoxycarbonyl.

Alkylthio in the context of the invention is a linear or branched alkyl radical which has 1 to 4 carbon atoms and is bonded via a sulfur atom. Preferred examples include: methylthio, ethylthio, n-propylthio, isopropylthio, 1-methylpropylthio, n-butylthio, iso-butylthio and tert-butylthio.

Alkylsulfonyl in the context of the invention is a straight-chain or branched alkyl radical which has 1 to 4 carbon atoms and is attached via a sulfonyl group. Preferred examples include: methylsulfonyl, ethylsulfonyl, n-propylsulfonyl, isopropylsulfonyl, n-butylsulfonyl and tert-butylsulfonyl.

4- to 7-membered heterocyclyl in the context of the invention is a monocyclic saturated heterocycle which has a total of 4 to 7 ring atoms, contains one or two ring heteroatoms from the group consisting of N, O, S, SO and/or $SO_2$ and is joined via a ring carbon atom or optionally a ring nitrogen atom. Examples include: azetidinyl, oxetanyl, pyrrolidinyl, pyrazolidinyl, tetrahydrofuranyl, piperidinyl, piperazinyl, tetrahydropyranyl, morpholinyl and thiomorpholinyl. Preference is given to: azetidinyl, oxetanyl, pyrrolidinyl, tetrahydrofuranyl, piperidinyl, piperazinyl, tetrahydropyranyl and morpholinyl.

5- to 7 membered heterocyclyl in the context of the invention is a partly unsaturated heterocycle which has a total of 5 to 7 ring atoms, contains 1 to 3 ring heteroatoms from the group of N, O, S and/or $SO_2$ and is fused to the phenyl ring in $R^3$. Examples include: dihydropyrrolyl, dihydroimidazolyl, dihydrothiazole dioxide, dihydrooxazolyl, dihydropyridyl, tetrahydropyrazinyl and dihydrooxazinyl.

Heteroaryl in the context of the invention is a monocyclic aromatic heterocycle (heteroaromatic) which has a total of 5 or 6 ring atoms, contains up to three identical or different ring heteroatoms from the group of N, O and/or S and is fused to the phenyl ring in $R^3$. Examples include: fury, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl and triazinyl. Preference is given to pyrazolyl, imidazolyl, thiazolyl and triazolyl.

Halogen in the context of the invention includes fluorine, chlorine, bromine and iodine. Preference is given to chlorine or fluorine.

An oxo group in the context of the invention is an oxygen atom bonded via a double bond to a carbon or sulfur atom.

In the formulae of the group that $R^2$ and $R^3$ may represent, the end point of the line marked by a symbol * or # or ## is not a carbon atom or a $CH_2$ group but is part of the bond to the respective atom to which $R^2$ and $R^3$ are bonded.

When radicals in the compounds of the general formula (I) are substituted, the radicals may be mono- or polysubstituted, unless specified otherwise. In the context of the present invention, all radicals which occur more than once are defined independently of one another. Substitution by one or two identical or different substituents is preferred. Very particular preference is given to substitution by one substituent.

In the context of the present invention, endometriosis is understood to mean an inflammatory disorder (Lousse J C et al., Front Biosci 4 (2012) 23-40] which is characterized by the growth of endometrial tissue (lesions) outside the Cavum uteri in the abdominal cavity.

In the context of the present invention, fibrosis is understood to mean a pathological new formation of connective tissue fibres. In principle, all tissue and organs can be affected.

In the context of the present invention, an adhesion is understood to mean a physical connection between organs which are not directly linked to one other in healthy humans. In principle, all tissue and organs can be affected.

In the context of the present invention, postoperative adhesion is understood to mean the physical connection between organs, resulting from physical intervention in the peritoneum such as a laparoscopy or laparotomy, for example in the context of endometriosis treatment or a tube ligation, which are not directly linked to one another in healthy humans. In principle, all tissue and organs can be affected.

In the context of the present invention, adenomyosis (adenomyosis uteri) is understood to mean a disorder in which endometrial cells lodge in the uterine muscle (myometrium) and settle in the middle layer of the uterine wall. The migrated endometrial cells are thus located, in addition to the cells of the inner endometrium, also in the overlying uterine muscle. This can lead to an enlargement and thickening of the uterus. These enlargements of the uterus may occur at a single point or distributed over the entire musculature of the uterus.

In the context of the present invention, secondary dysmenorrhoea is understood to mean secondary period pain, triggered by organic changes or disorders such as endometriosis or adhesions.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

In the context of the present invention, preference is given to the use of compounds of the formula (I), in which $R^1$ is hydrogen, methyl or ethyl, $R^2$ is a group of the formula

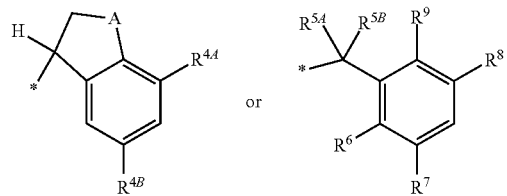

where
* is the point of attachment to the uracil nitrogen atom,
A is —$CH_2$— or oxygen,
$R^{4A}$ is hydrogen, fluorine, chlorine, trifluoromethyl or methyl,
$R^{4B}$ is hydrogen, fluorine, chlorine, trifluoromethyl or methyl, with the proviso that at least one of the $R^{4A}$ and $R^{4B}$ radicals is not hydrogen,
$R^{5A}$ is hydrogen,
$R^{5B}$ is hydrogen,
$R^6$ is hydrogen,
$R^7$ is hydrogen,
$R^8$ is fluorine, chlorine, difluoromethyl, trifluoromethyl or methyl,
$R^9$ is fluorine, chlorine, difluoromethyl, trifluoromethyl or methyl,
$R^3$ is a group of the formula where
# is the point of attachment to the uracil nitrogen atom,
$E^1$ is $CR^{11}$ or N,
  in which
  $R^{11}$ is hydrogen, ($C_1$-$C_4$)-alkyl, ($C_3$-$C_7$)-cycloalkyl or aminocarbonyl,
$E^2$ is $CR^{12}$ or N,
  in which
  $R^{12}$ is hydrogen, ($C_1$-$C_4$)-alkyl or ($C_3$-$C_7$)-cycloalkyl,
$E^3$ is $NR^{14}$ or S,
  in which
  $R^{14}$ is hydrogen, ($C_1$-$C_4$)-alkyl or ($C_3$-$C_7$)-cycloalkyl,
$G^1$ is C=O or $SO_2$,
$G^2$ is $CR^{16A}R^{16B}$, $NR^{17}$, O or S,
  in which
  $R^{16A}$ is hydrogen, fluorine, ($C_1$-$C_4$)-alkyl or hydroxy,
  $R^{16B}$ is hydrogen, fluorine, chlorine, ($C_1$-$C_4$)-alkyl or trifluoromethyl,
  or
  $R^{16A}$ and $R^{16B}$ together with the carbon atom to which they are bonded form a 3- to 6-membered carbocycle,
$R^{17}$ is hydrogen, ($C_1$-$C_6$)-alkyl, ($C_3$-$C_7$)-cycloalkyl or ($C_1$-$C_4$)-alkoxycarbonyl,
  in which ($C_1$-$C_6$)-alkyl may be substituted by 1 to 3 substituents independently selected from the group of fluorine, trifluoromethyl, cyano, ($C_3$-$C_7$)-cycloalkyl, hydroxyl, trifluoromethoxy, ($C_1$-$C_4$)-alkoxy, azetidinyl, oxetanyl, tetrahydrofuranyl and pyrrolidinyl,
$G^3$ is $CR^{18A}R^{18B}$, $NR^{19}$, O or S,
  in which
  $R^{18A}$ is hydrogen, fluorine, ($C_1$-$C_4$)-alkyl or hydroxy,
  $R^{18B}$ is hydrogen, fluorine, chlorine, ($C_1$-$C_4$)-alkyl or trifluoromethyl,
  or
  $R^{18A}$ and $R^{18B}$ together with the carbon atom to which they are bonded form a 3- to 6-membered carbocycle,
  $R^{19}$ is hydrogen, ($C_1$-$C_6$)-alkyl, ($C_3$-$C_7$)-cycloalkyl or ($C_1$-$C_4$)-alkoxycarbonyl,
    in which ($C_1$-$C_6$)-alkyl may be substituted by 1 to 3 substituents independently selected from the group of fluorine, trifluoromethyl, cyano, ($C_3$-$C_7$)-cycloalkyl, hydroxyl, trifluoromethoxy, ($C_1$-$C_4$)-alkoxy, azetidinyl, oxetanyl, tetrahydrofuranyl and pyrrolidinyl,
$G^4$ is $CH_2$, C=O or $SO_2$,
$K^1$ is $CH_2$ or O,
$K^2$ is $CH_2$ or O,
with the proviso that only one of the $K^1$ and $K^2$ groups is O,
$D^1$, $D^2$, $D^3$ and $D^4$ are each independently $CR^{23}$ or N,
  in which
  $R^{23}$ is hydrogen, halogen, ($C_1$-$C_6$)-alkyl or ($C_3$-$C_7$)-cycloalkyl,
with the proviso that not more than 2 of the $D^1$, $D^2$, $D^3$ and $D^4$ groups are N,
$R^{24}$ is fluorine or methyl,
n is a number 0 or 1,
$R^{10}$ is ($C_1$-$C_4$)-alkyl or ($C_3$-$C_7$)-cycloalkyl,
  in which ($C_1$-$C_4$)-alkyl may be substituted by 1 or 2 substituents independently selected from the group of fluorine, trifluoromethyl, cyclopropyl, cyclobutyl, hydroxyl, methoxy, ethoxy, azetidinyl, oxetanyl, tetrahydrofuranyl and pyrrolidinyl,
$R^{13}$ is hydrogen, ($C_1$-$C_4$)-alkyl or ($C_3$-$C_7$)-cycloalkyl,
$R^{15}$ is hydrogen, ($C_1$-$C_6$)-alkyl or ($C_3$-$C_7$)-cycloalkyl,
  in which ($C_1$-$C_6$)-alkyl may be substituted by 1 or 2 substituents independently selected from the group of fluorine, trifluoromethyl, cyclopropyl, cyclobutyl, hydroxyl, methoxy, ethoxy, azetidinyl, oxetanyl, tetrahydrofuranyl and pyrrolidinyl,
$R^{20}$ is hydrogen, ($C_1$-$C_6$)-alkyl, ($C_3$-$C_7$)-cycloalkyl or ($C_1$-$C_4$)-alkylcarbonyl,
  in which ($C_1$-$C_6$)-alkyl may be substituted by 1 or 2 substituents independently selected from the group of fluorine, trifluoromethyl, cyclopropyl, cyclobutyl, hydroxyl, methoxy, ethoxy, azetidinyl, oxetanyl, tetrahydrofuranyl and pyrrolidinyl,
$R^{21}$ is hydrogen, ($C_1$-$C_6$)-alkyl, ($C_3$-$C_7$)-cycloalkyl or ($C_1$-$C_4$)-alkylsulfonyl,
$R^{22A}$ is hydrogen or $C_1$-$C_4$-alkyl,
$R^{22B}$ is hydrogen or $C_1$-$C_4$-alkyl,
or $R^{22A}$ and $R^{22B}$ together with the carbon atom to which they are bonded form a carbonyl group, and salts, solvates and solvates of the salts thereof for the treatment and prevention of endometriosis, of endometriosis-associated fibrosis, of adenomyosis, of pain associated with an endometriosis disorder and the treatment and prevention of postoperative fibroses and adhesions.

In a further embodiment of the invention, the compounds are suitable for use in the treatment of endometriosis, of endometriosis-associated fibrosis, of adenomyosis and of pain associated with an endometriosis disorder, of endometriosis-associated adhesions and fibroses, of endometriosis-associated symptoms such as dysmenorrhoea, dyspareunia, dysuria or dyschezia and also of endometriosis-associated subfertility.

In a further embodiment of the invention, the compounds are suitable for use in the treatment and prevention of postoperative adhesions in the abdominal cavity and to prevent subfertility caused by adhesions.

In a further embodiment of the invention, the compounds are suitable for the treatment of Dupuytren's contracture (a disorder of the connective tissue of the palms) and in the treatment and/or prophylaxis of chronic pain in the pelvic cavity.

In the context of the present invention, preference is also given to the use of compounds of the formula (I), in which $R^1$ is hydrogen, methyl or ethyl, $R^2$ is a group of the formula

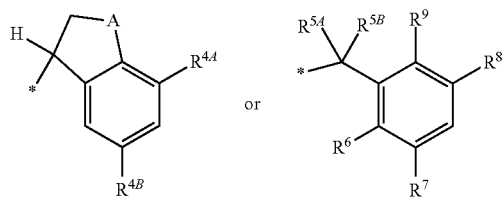

where

* is the point of attachment to the uracil nitrogen atom,

A is —CH$_2$—, —CH$_2$—CH$_2$—, —O—CH$_2$-## or oxygen, in which ## is the point of attachment to the phenyl ring, $R^{4A}$ is hydrogen, fluorine, chlorine, trifluoromethyl or methyl, $R^{4B}$ is hydrogen, fluorine, chlorine, trifluoromethyl or methyl, with the proviso that at least one of the $R^{4A}$ and $R^{4B}$ radicals is not hydrogen, $R^{5A}$ is hydrogen, $R^{5B}$ is hydrogen, $R^6$ is hydrogen, $R^7$ is hydrogen, $R^8$ is fluorine, chlorine, difluoromethyl, trifluoromethyl or methyl, $R^9$ is fluorine, chlorine, difluoromethyl, trifluoromethyl or methyl, $R^3$ is a group of the formula

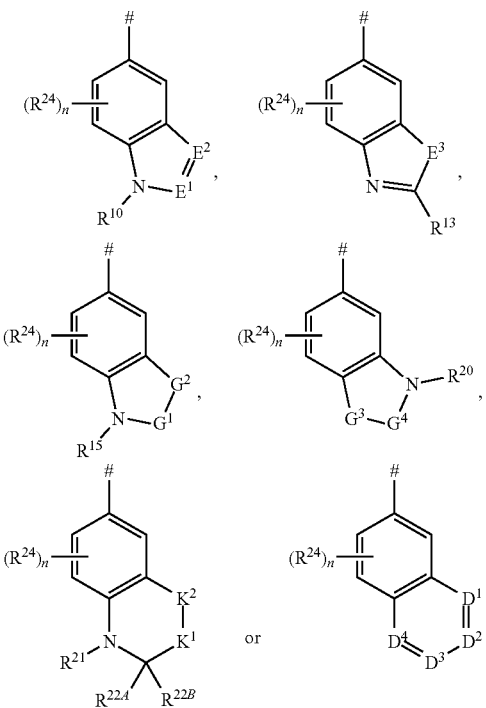

where

\# is the point of attachment to the uracil nitrogen atom, $E^1$ is $CR^{11}$ or N, in which $R^{11}$ is hydrogen, (C$_1$-C$_4$)-alkyl, (C$_3$-C$_7$)-cycloalkyl or aminocarbonyl, $E^2$ is $CR^{12}$ or N, in which $R^{12}$ is hydrogen, (C$_1$-C$_4$)-alkyl or (C$_3$-C$_7$)-cycloalkyl, $E^3$ is $NR^{14}$ or S, in which $R^{14}$ is hydrogen, (C$_1$-C$_4$)-alkyl or (C$_3$-C$_7$)-cycloalkyl, $G^1$ is C=O or SO$_2$, $G^2$ is $CR^{16A}R^{16B}$, $NR^{17}$, O or S, in which $R^{16A}$ is hydrogen, fluorine, (C$_1$-C$_4$)-alkyl or hydroxy, $R^{16B}$ is hydrogen, fluorine, chlorine, (C$_1$-C$_4$)-alkyl or trifluoromethyl, or $R^{16A}$ and $R^{16B}$ together with the carbon atom to which they are bonded form a 3- to 6-membered carbocycle, $R^{17}$ is hydrogen, (C$_1$-C$_6$)-alkyl, (C$_3$-C$_7$)-cycloalkyl or (C$_1$-C$_4$)-alkoxycarbonyl, in which (C$_1$-C$_6$)-alkyl may be substituted by 1 to 3 substituents independently selected from the group of fluorine, trifluoromethyl, cyano, (C$_3$-C$_7$)-cycloalkyl, hydroxyl, trifluoromethoxy, (C$_1$-C$_4$)-alkoxy, azetidinyl, oxetanyl, tetrahydrofuranyl and pyrrolidinyl, $G^3$ is $CR^{18A}R^{18B}$, $NR^{19}$, O or S, in which $R^{18A}$ is hydrogen, fluorine, (C$_1$-C$_4$)-alkyl or hydroxy, $R^{18B}$ is hydrogen, fluorine, chlorine, (C$_1$-C$_4$)-alkyl or trifluoromethyl, or $R^{18A}$ and $R^{18B}$ together with the carbon atom to which they are bonded form a 3- to 6-membered carbocycle, $R^{19}$ is hydrogen, $(C_1-C_6)$-alkyl, $(C_3-C_7)$-cycloalkyl or $(C_1-C_4)$-alkoxycarbonyl,
in which $(C_1-C_6)$-alkyl may be substituted by 1 to 3 substituents independently selected from the group of fluorine, trifluoromethyl, cyano, $(C_3-C_7)$-cycloalkyl, hydroxyl, trifluoromethoxy, $(C_1-C_4)$-alkoxy, azetidinyl, oxetanyl, tetrahydrofuranyl and pyrrolidinyl, $G^4$ is $CH_2$, C=O or $SO_2$, $K^1$ is $CH_2$ or O, $K^2$ is $CH_2$ or O, with the proviso that only one of the $K^1$ and $K^2$ groups is O, $D^1$, $D^2$, $D^3$ and $D^4$ are each independently $CR^{23}$ or N,
in which
$R^{23}$ is hydrogen, halogen, $(C_1-C_6)$-alkyl or $(C_3-C_7)$-cycloalkyl, with the proviso that not more than 2 of the $D^1$, $D^2$, $D^3$ and $D^4$ groups are N, $R^{24}$ is fluorine or methyl, n is a number 0 or 1, $R^{10}$ is $(C_1-C_4)$-alkyl or $(C_3-C_7)$-cycloalkyl,
in which $(C_1-C_4)$-alkyl may be substituted by 1 or 2 substituents independently selected from the group of fluorine, trifluoromethyl, cyclopropyl, cyclobutyl, hydroxyl, methoxy, ethoxy, azetidinyl, oxetanyl, tetrahydrofuranyl and pyrrolidinyl, $R^{13}$ is hydrogen, $(C_1-C_4)$-alkyl or $(C_3-C_7)$-cycloalkyl, $R^{15}$ is hydrogen, $(C_1-C_6)$-alkyl or $(C_3-C_7)$-cycloalkyl,
in which $(C_1-C_6)$-alkyl may be substituted by 1 or 2 substituents independently selected from the group of fluorine, trifluoromethyl, cyclopropyl, cyclobutyl, hydroxyl, methoxy, ethoxy, azetidinyl, oxetanyl, tetrahydrofuranyl and pyrrolidinyl, $R^{20}$ is hydrogen, $(C_1-C_6)$-alkyl, $(C_3-C_7)$-cycloalkyl or $(C_1-C_4)$-alkylcarbonyl,
in which $(C_1-C_6)$-alkyl may be substituted by 1 or 2 substituents independently selected from the group of fluorine, trifluoromethyl, cyclopropyl, cyclobutyl, hydroxyl, methoxy, ethoxy, azetidinyl, oxetanyl, tetrahydrofuranyl and pyrrolidinyl, $R^{21}$ is hydrogen, $(C_1-C_6)$-alkyl, $(C_3-C_7)$-cycloalkyl or $(C_1-C_4)$-alkylsulfonyl, $R^{22A}$ is hydrogen or $C_1-C_4$-alkyl, $R^{22B}$ is hydrogen or $C_1-C_4$-alkyl,
or $R^{22A}$ and $R^{22B}$ together with the carbon atom to which they are bonded form a carbonyl group and salts, solvates and solvates of the salts thereof for the treatment and prevention of endometriosis, of endometriosis-associated fibrosis, of adenomyosis, of pain associated with an endometriosis disorder and the treatment and prevention of postoperative fibroses and adhesions.

In a further embodiment of the invention, the compounds are suitable for use in the treatment of endometriosis, of endometriosis-associated fibrosis, of adenomyosis and of pain associated with an endometriosis disorder, of endometriosis-associated adhesions and fibroses, of endometriosis-associated symptoms such as dysmenorrhoea, dyspareunia, dysuria or dyschezia and also of endometriosis-associated subfertility.

In a further embodiment of the invention, the compounds are suitable for use in the treatment and prevention of postoperative adhesions in the abdominal cavity and to prevent subfertility caused by adhesions.

In a further embodiment of the invention, the compounds are suitable for the treatment of Dupuytren's contracture (a disorder of the connective tissue of the palms) and in the treatment and/or prophylaxis of chronic pain in the pelvic cavity.

In the context of the present invention, particular preference is given to the use of compounds of the formula (I), in which $R^1$ is hydrogen, $R^2$ is a group of the formula

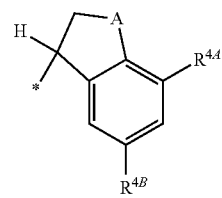

where

\* is the point of attachment to the uracil nitrogen atom,

A is —$CH_2$—, $R^{4A}$ is chlorine or trifluoromethyl, $R^{4B}$ is hydrogen, $R^3$ is a group of the formula

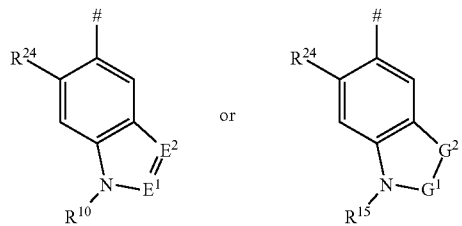

where

\# is the point of attachment to the uracil nitrogen atom, $E^1$ is $CR^{11}$,
in which
$R^{11}$ is hydrogen, $E^2$ is N, $G^1$ is C=O, $G^2$ is $CR^{16A}R^{16B}$, $NR^{17}$, O or S,
in which
$R^{16A}$ is hydrogen, fluorine, methyl or hydroxy,
$R^{16B}$ is hydrogen, fluorine, methyl or trifluoromethyl,
or
$R^{16A}$ and $R^{16B}$ together with the carbon atom to which they are bonded form a cyclopropyl ring, $R^{17}$ is hydrogen, $(C_1-C_4)$-alkyl or $(C_3-C_5)$-cycloalkyl,
in which $(C_1-C_4)$-alkyl may be substituted by 1 to 3 substituents independently selected from the group of fluorine, trifluoromethyl, cyano, cyclopropyl, cyclobutyl, hydroxyl, trifluoromethoxy, methoxy, ethoxy, azetidinyl, oxetanyl, tetrahydrofuranyl and pyrrolidinyl, $R^{24}$ is hydrogen or fluorine, $R^{10}$ is $(C_1-C_4)$-alkyl, $R^{15}$ is hydrogen, methyl or ethyl,
in which methyl and ethyl may be substituted by 1 substituent selected from the group of fluorine, trifluoromethyl and cyclopropyl, and salts, solvates and solvates of the salts thereof for the treatment and prevention of endometriosis, of endometriosis-associated fibrosis, of adenomyosis, of pain associated with an endometriosis disorder and the treatment and prevention of postoperative fibroses and adhesions.

In a further embodiment of the invention, the compounds are suitable for use in the treatment of endometriosis, of endometriosis-associated fibrosis, of adenomyosis and of pain associated with an endometriosis disorder, of endometriosis-associated adhesions and fibroses, of endometriosis-associated symptoms such as dysmenorrhoea, dyspareunia, dysuria or dyschezia and also of endometriosis-associated subfertility.

In a further embodiment of the invention, the compounds are suitable for use in the treatment and prevention of postoperative adhesions in the abdominal cavity and to prevent subfertility caused by adhesions.

In a further embodiment of the invention, the compounds are suitable for the treatment of Dupuytren's contracture (a disorder of the connective tissue of the palms) and in the treatment and/or prophylaxis of chronic pain in the pelvic cavity.

In the context of the present invention, preference is also given to the use of compounds of the formula (I), in which
$R^1$ is hydrogen,
$R^2$ is a group of the formula

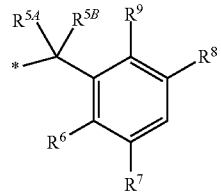

where
* is the point of attachment to the uracil nitrogen atom,
$R^{5A}$ is hydrogen,
$R^{5B}$ is hydrogen,
$R^6$ is hydrogen,
$R^7$ is hydrogen,
$R^8$ is fluorine, chlorine or trifluoromethyl,
$R^9$ is fluorine, chlorine, trifluoromethyl or methyl,
$R^3$ is a group of the formula

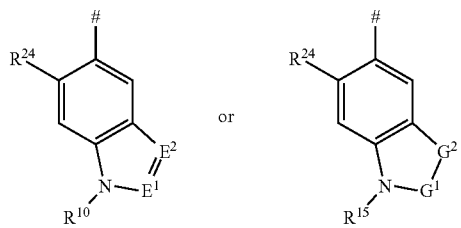

where
# is the point of attachment to the uracil nitrogen atom,
$E^1$ is $CR^{11}$,
  in which
  $R^{11}$ is hydrogen,
$E^2$ is N,
$G^1$ is C=O,
$G^2$ is $CR^{16A}R^{16B}$, $NR^{17}$, O or S,
  in which
  $R^{16A}$ is hydrogen, fluorine, methyl or hydroxy,
  $R^{16B}$ is hydrogen, fluorine, methyl or trifluoromethyl,
  or $R^{16A}$ and $R^{16B}$ together with the carbon atom to which they are bonded form a cyclopropyl ring,
$R^{17}$ is hydrogen, $(C_1-C_4)$-alkyl or $(C_3-C_5)$-cycloalkyl,
  in which $(C_1-C_4)$-alkyl may be substituted by 1 to 3 substituents independently selected from the group of fluorine, trifluoromethyl, cyano, cyclopropyl, cyclobutyl, hydroxyl, trifluoromethoxy, methoxy, ethoxy, azetidinyl, oxetanyl, tetrahydrofuranyl and pyrrolidinyl,
$R^{24}$ is hydrogen or fluorine,
$R^{10}$ is $(C_1-C_4)$-alkyl,
$R^{15}$ is hydrogen, methyl or ethyl,
  in which methyl and ethyl may be substituted by 1 substituent selected from the group of fluorine, trifluoromethyl and cyclopropyl,
and salts, solvates and solvates of the salts thereof for the treatment and prevention of endometriosis, of endometriosis-associated fibrosis, of adenomyosis, of pain associated with an endometriosis disorder and the treatment and prevention of postoperative fibroses and adhesions.

In a further embodiment of the invention, the compounds are suitable for use in the treatment of endometriosis, of endometriosis-associated fibrosis, of adenomyosis and of pain associated with an endometriosis disorder, of endometriosis-associated adhesions and fibroses, of endometriosis-associated symptoms such as dysmenorrhoea, dyspareunia, dysuria or dyschezia and also of endometriosis-associated subfertility.

In a further embodiment of the invention, the compounds are suitable for use in the treatment and prevention of postoperative adhesions in the abdominal cavity and to prevent subfertility caused by adhesions.

In a further embodiment of the invention, the compounds are suitable for the treatment of Dupuytren's contracture (a disorder of the connective tissue of the palms) and in the treatment and/or prophylaxis of chronic pain in the pelvic cavity.

In the context of the present invention, preference is also given to the use of compounds of the formula (I), in which
$R^1$ is hydrogen, methyl or ethyl,
$R^2$ is a group of the formula

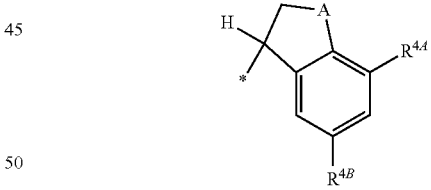

where
* is the point of attachment to the uracil nitrogen atom,
A is —$CH_2$—,
$R^{4A}$ is chlorine or trifluoromethyl,
$R^{4B}$ is hydrogen,
and salts, solvates and solvates of the salts thereof for the treatment and prevention of endometriosis, of endometriosis-associated fibrosis, of adenomyosis, of pain associated with an endometriosis disorder and the treatment and prevention of postoperative fibroses and adhesions.

In a further embodiment of the invention, the compounds are suitable for use in the treatment of endometriosis, of endometriosis-associated fibrosis, of adenomyosis and of pain associated with an endometriosis disorder, of endometriosis-associated adhesions and fibroses, of endometriosis-associated symptoms such as dysmenorrhoea, dyspareunia, dysuria or dyschezia and also of endometriosis-associated subfertility.

In a further embodiment of the invention, the compounds are suitable for use in the treatment and prevention of postoperative adhesions in the abdominal cavity and to prevent subfertility caused by adhesions.

In a further embodiment of the invention, the compounds are suitable for the treatment of Dupuytren's contracture (a disorder of the connective tissue of the palms) and in the treatment and/or prophylaxis of chronic pain in the pelvic cavity.

In the context of the present invention, preference is also given to the use of compounds of the formula (I), in which
$R^3$ is a group of the formula

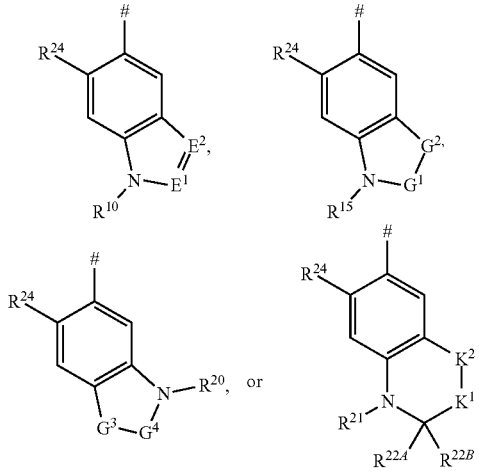

where
# is the point of attachment to the uracil nitrogen atom,
$E^1$ is $CR^{11}$ or N,
in which
$R^{11}$ is hydrogen, methyl, ethyl or aminocarbonyl,
$E^2$ is $CR^{12}$ or N,
in which
$R^{12}$ is hydrogen,
$G^1$ is C=O or $SO_2$,
$G^2$ is $CR^{16A}R^{16B}$, $NR^{17}$, O or S,
in which
$R^{16A}$ is hydrogen, fluorine, methyl or hydroxy,
$R^{16B}$ is hydrogen, fluorine, chlorine, methyl or trifluoromethyl,
or
$R^{16A}$ and $R^{16B}$ together with the carbon atom to which they are bonded form a cyclopropyl ring,
$R^{17}$ is hydrogen, $(C_1-C_4)$-alkyl, cyclopropyl or cyclobutyl,
in which $(C_1-C_4)$-alkyl may be substituted by 1 or 2 substituents independently selected from the group of fluorine, trifluoromethyl, cyclopropyl, cyclobutyl, hydroxyl, azetidinyl and oxetanyl,
$G^3$ is $CR^{18A}R^{18B}$
in which
$R^{18A}$ is hydrogen, fluorine, methyl or hydroxy,
$R^{18B}$ is hydrogen, fluorine, methyl or trifluoromethyl,
$G^4$ is C=O,
$K^1$ is $CH_2$ or O,
$K^2$ is $CH_2$,
$R^{24}$ is hydrogen, fluorine or methyl,
$R^{10}$ is methyl or ethyl,
$R^{15}$ is methyl or ethyl,
$R^{20}$ is hydrogen, methyl, ethyl or methylcarbonyl,
$R^{21}$ is methyl or ethyl,
$R^{22A}$ and $R^{22B}$ together with the carbon atom to which they are bonded form a carbonyl group,
and salts, solvates and solvates of the salts thereof for the treatment and prevention of endometriosis, of endometriosis-associated fibrosis, of adenomyosis, of pain associated with an endometriosis disorder and the treatment and prevention of postoperative fibroses and adhesions.

In a further embodiment of the invention, the compounds are suitable for use in the treatment of endometriosis, of endometriosis-associated fibrosis, of adenomyosis and of pain associated with an endometriosis disorder, of endometriosis-associated adhesions and fibroses, of endometriosis-associated symptoms such as dysmenorrhoea, dyspareunia, dysuria or dyschezia and also of endometriosis-associated subfertility.

In a further embodiment of the invention, the compounds are suitable for use in the treatment and prevention of postoperative adhesions in the abdominal cavity and to prevent subfertility caused by adhesions.

In a further embodiment of the invention, the compounds are suitable for the treatment of Dupuytren's contracture (a disorder of the connective tissue of the palms) and in the treatment and/or prophylaxis of chronic pain in the pelvic cavity.

In the context of the present invention, preference is also given to the use of compounds of the formula (I), in which
$R^2$ is a group of the formula

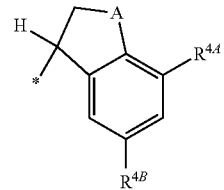

where
* is the point of attachment to the uracil nitrogen atom,
A is —$CH_2$—,
$R^{4A}$ is chlorine or trifluoromethyl,
$R^{4B}$ is hydrogen,
and the carbon atom bonded to the uracil nitrogen atom has R configuration,
and salts, solvates and solvates of the salts thereof for the treatment and prevention of endometriosis, of endometriosis-associated fibrosis, of adenomyosis, of pain associated with an endometriosis disorder and the treatment and prevention of postoperative fibroses and adhesions.

In a further embodiment of the invention, the compounds are suitable for use in the treatment of endometriosis, of endometriosis-associated fibrosis, of adenomyosis and of pain associated with an endometriosis disorder, of endometriosis-associated adhesions and fibroses, of endometriosis-associated symptoms such as dysmenorrhoea, dyspareunia, dysuria or dyschezia and also of endometriosis-associated subfertility.

In a further embodiment of the invention, the compounds are suitable for use in the treatment and prevention of postoperative adhesions in the abdominal cavity and to prevent subfertility caused by adhesions.

In a further embodiment of the invention, the compounds are suitable for the treatment of Dupuytren's contracture (a disorder of the connective tissue of the palms) and in the treatment and/or prophylaxis of chronic pain in the pelvic cavity.

In the context of the present invention, preference is also given to the use of compounds of the formula (I), in which
R² is a group of the formula

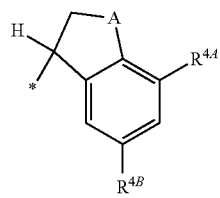

where
* is the point of attachment to the uracil nitrogen atom,
A is —CH₂—,
R⁴ᴬ is hydrogen, fluorine, chlorine, trifluoromethyl or methyl,
R⁴ᴮ is hydrogen, fluorine, chlorine, trifluoromethyl or methyl,
with the proviso that at least one of the R⁴ᴬ and R⁴ᴮ radicals is not hydrogen,
and the carbon atom bonded to the uracil nitrogen atom has R configuration,
and salts, solvates and solvates of the salts thereof for the treatment and prevention of endometriosis, of endometriosis-associated fibrosis, of adenomyosis, of pain associated with an endometriosis disorder and the treatment and prevention of postoperative fibroses and adhesions.

In a further embodiment of the invention, the compounds are suitable for use in the treatment of endometriosis, of endometriosis-associated fibrosis, of adenomyosis and of pain associated with an endometriosis disorder, of endometriosis-associated adhesions and fibroses, of endometriosis-associated symptoms such as dysmenorrhoea, dyspareunia, dysuria or dyschezia and also of endometriosis-associated subfertility.

In a further embodiment of the invention, the compounds are suitable for use in the treatment and prevention of postoperative adhesions in the abdominal cavity and to prevent subfertility caused by adhesions.

In a further embodiment of the invention, the compounds are suitable for the treatment of Dupuytren's contracture (a disorder of the connective tissue of the palms) and in the treatment and/or prophylaxis of chronic pain in the pelvic cavity.

The compounds of the general formula (I) can be used alone or, if required, in combination with other active ingredients.

Therefore, the invention furthermore relates also to use of the chymase inhibitors of the general formula (I) and also salts, solvates and solvates of the salts thereof in combination with other active ingredients for the treatment and prevention of endometriosis, of endometriosis-associated fibrosis, of adenomyosis, of pain associated with an endometriosis disorder and the treatment and prevention of postoperative fibroses and adhesions.

In a further embodiment of the invention, the compounds are suitable for use in the treatment of endometriosis, of endometriosis-associated fibrosis, of adenomyosis and of pain associated with an endometriosis disorder, of endometriosis-associated adhesions and fibroses, of endometriosis-associated symptoms such as dysmenorrhoea, dyspareunia, dysuria or dyschezia and also of endometriosis-associated subfertility.

In a further embodiment of the invention, the compounds of the general formula (I), and also salts, solvates and solvates of the salts thereof, in combination with other active ingredients are suitable for use in the treatment and prevention of postoperative adhesions in the abdominal cavity and for the prevention of subfertility caused by adhesions.

In a further embodiment of the invention, the compounds of the general formula (I), and also salts, solvates and solvates of the salts thereof, in combination with other active ingredients are suitable for the treatment of Dupuytren's contracture (a disorder of the connective tissue of the palms) and in the treatment and/or prophylaxis of chronic pain in the pelvic cavity.

Suitable active ingredients, which may be used in combination with the chymase inhibitors according to general formula (I), are cited in the following by way of example in a non-limiting manner: known hormonal agents such as progestins, e.g. norethynodrel, norethindrone, norethindrone acetate, ethynodiol acetate, norgestrel, levonorgestrel, norgestimate, desogestrel, gestodene, drospirenone, dienogest or nomegestrol acetate, alone or together with oestrogens, e.g. ethinylestradiol, estradiol or estradiol esters such as estradiol valerate; the combination with hormonal contraceptives is also possible in this case, which may be administered either by the oral, subcutaneous, transdermal, intrauterine or intravaginal routes.

Suitable preparations for this purpose are combined oral contraceptives (COC), progestin only pills (POP), which contain only a progestin or hormone-containing devices such as implants, patches or intravaginal rings.

Examples of COCs include a combination of an oestrogen (estradiol) and a gestagen (progestin). The oestrogenic component in most COCs is ethinylestradiol. Some COCs comprise estradiol or estradiol valerate. The following progestins are used in COCs: norethynodrel, norethindrone, norethindrone acetate, ethynodiol acetate, norgestrel, levonorgestrel, norgestimate, desogestrel, gestodene, drospirenone, dienogest or nomegestrol acetate.

A further embodiment of the present invention is therefore a combination of COC with the present compounds of the general formula (I), for example combinations of the compounds of the general formula (I) with ethinylestradiol and drospirenone (Yasmin® and Yaz®), with ethinylestradiol and levonorgestrel (Microgynon® and Miranove), with ethinylestradiol and desogestrel (Marvelon®), with ethinylestradiol and dienogest (Valette) or ethinylestradiol with chlormadinone acetate (Belara® and Enriqe). A further embodiment of the present invention is a combination of compounds of the general formula (I) with, for example, estradiol and normegestrol (Zoely®) or estradiol valerate and dienogest (Qlaire®).

A further embodiment is the administration of compounds of the general formula (I) in combination with synthetic progestins without an oestrogen component. This variant can be achieved, for example, using so-called POPs (Progestin—Only Pills) as contraceptives. POPs are also known as mini pills. Examples of POPs are Cerazette® with the progestin desogestrel, Microlut® with levonorgestrel or Micronor® with norethindrone.

A further embodiment of the present invention includes a combination of the compounds of the general formula (I) with non-oral progestin-only forms, such as intrauterine devices (IUDs), e.g. Mirena®, Jaydess® or Kyleena® each with levonorgestrel, or such as injectable forms, e.g. Depo-Provera® with medroxyprogesterone acetate, or such as implants, e.g. Implanon with etonogestrel.

Further hormone-containing forms with contraceptive effect, which may be combined with the compounds of the general formula (I), are vaginal rings such as NuvaRing® with ethinylestradiol and etonogestrel or vaginal rings comprising an aromatase inhibitor, for example anastrozole, and a gestagen, or transdermal systems such as contraceptive patches, e.g. Ortho-Evra with ethinylestradiol and norelgestromin or Apleek (Lisvy) with ethinylestradiol and gestodene.

Furthermore, in the context of the present invention, the compounds of the general formula (I) may be used in combination with the following active ingredients: combination with inhibitors of the P2X purine receptors (P2X3, P2X4), with inhibitors of IRAK4 (interleukin-1 receptor-associated kinase 4), PTGES (prostaglandin-E synthase) and antagonists of the prostaglandin receptor EP4 (prostaglandin E2 receptor 4). Further combinations are with AKR1C3 inhibitors (aldo-keto reductase 1C3) and with function-blocking antibodies of the prolactin receptor.

The combinations cited are suitable for use in the treatment of inflammatory and various fibrotic disorders, particularly for the treatment and prevention of endometriosis, of endometriosis-associated fibrosis, of adenomyosis, of pain associated with an endometriosis disorder and the treatment and prevention of postoperative fibroses and adhesions.

In a further embodiment of the invention, the combinations cited are suitable for use in the treatment of endometriosis, of endometriosis-associated fibrosis, of adenomyosis and of pain associated with an endometriosis disorder, of endometriosis-associated adhesions and fibroses, of endometriosis-associated symptoms such as dysmenorrhoea, dyspareunia, dysuria or dyschezia and also of endometriosis-associated subfertility.

In a further embodiment of the invention, the combinations cited are suitable for use in the treatment and prevention of postoperative adhesions in the abdominal cavity and to prevent subfertility caused by adhesions.

In a further embodiment of the invention, the combinations cited are suitable for the treatment of Dupuytren's contracture (a disorder of the connective tissue of the palms) and in the treatment and/or prophylaxis of chronic pain in the pelvic cavity.

The compounds of the general formula (I) can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds of the general formula (I) can be administered in administration forms suitable for these administration routes.

Suitable administration forms for oral administration are those which work according to the prior art and release the compounds of the invention rapidly and/or in a modified manner and which contain the compounds of the invention in crystalline and/or amorphized and/or dissolved form, for example tablets (uncoated or coated tablets, for example with gastric juice-resistant or retarded-dissolution or insoluble coatings which control the release of the compound of the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can bypass an absorption step (e.g. take place intravenously, intraarterially, intracardially, intraspinally or intralumbally) or include an absorption (e.g. take place inhalatively, intramuscularly, subcutaneously, intracutaneously, percutaneously or intraperitoneally). Administration forms suitable for parenteral administration include inter alia preparations for injection and infusion in the form of solutions, suspensions, emulsions, lyophilizates or sterile powders.

For the other administration routes, suitable examples are inhalation medicaments (including powder inhalers, nebulizers, aerosols), nasal drops, solutions or sprays; tablets for lingual, sublingual or buccal administration, films/oblates or capsules, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, dusting powders, implants or stents.

Oral and parenteral administration are preferred, especially oral, intravenous and inhalative administration.

The compounds of the general formula (I) can be converted into the administration forms mentioned. This can be done in a manner known per se, by mixing with inert, nontoxic, pharmaceutically suitable excipients. These excipients include inter alia carriers (for example microcrystalline cellulose, lactose, mannitol), solvents (e.g. liquid polyethylene glycols), emulsifiers and dispersing or wetting agents (for example sodium dodecylsulfate, polyoxysorbitan oleate), binders (for example polyvinylpyrrolidone), synthetic and natural polymers (for example albumin), stabilizers (e.g. antioxidants, for example ascorbic acid), colourants (e.g. inorganic pigments, for example iron oxides) and flavour and/or odour correctors.

In general, it has been found to be advantageous in the case of oral administration to administer amounts of about 0.001 to 1 mg/kg, preferably about 0.01 to 0.5 mg/kg body weight to achieve effective results. In the case of oral administration the dosage is about 0.01 to 100 mg/kg, preferably about 0.01 to 20 mg/kg and most preferably 0.1 to 10 mg/kg body weight.

It may nevertheless be necessary in some cases to deviate from the stated amounts, and specifically as a function of body weight, route of administration, individual response to the active ingredient, nature of the preparation and time at which or interval over which administration takes place. Thus in some cases it may be sufficient to manage with less than the abovementioned minimum amount, while in other cases the upper limit mentioned must be exceeded. In the case of administration of greater amounts, it may be advisable to divide them into several individual doses over the day.

The working examples which follow illustrate the invention. The invention is not restricted to the examples.

Unless stated otherwise, the percentages in the tests and examples which follow are percentages by weight; parts are parts by weight. Solvent ratios, dilution ratios and concentration data for liquid/liquid solutions, unless indicated otherwise, are based in each case on volume.

EXPERIMENTAL SECTION

The synthesis of the compounds of the general formula (I) is described in WO2013/167495 A1.

Assessment of the Pharmacological Activity

The pharmacological activity of the compounds according to the invention on chymase is shown in the assays described in WO2013/167495 A1.

For the sake of completeness, the results of the enzymatic chymase assay are listed here again.

Enzymatic Chymase Assay (WO2013/167495)

The enzyme source used is recombinant human chymase (expressed in HEK293 cells) or chymase purified from hamsters' tongues. The substrate used for chymase is Abz-HPFHL-Lys(Dnp)-NH2. For the assay, 1 μl of a 50-fold concentrated solution of test substance in DMSO, 24 μl of enzyme solution (dilution 1:80 000 human or 1:4000 hamster) and 25 μl of substrate solution (final concentration 10 μM) in assay buffer (Tris 50 mM (pH 7.5), sodium chloride 150 mM, BSA 0.10%, Chaps 0.10%, glutathione 1 mM, EDTA 1 mM) were combined in a white 384-well microtitre plate (Greiner Bio-One, Frickenhausen, Germany). The reaction is incubated at 32 degrees for 60 min and the fluorescence emission at 465 nm after excitation at 340 nm is measured in a fluorescence reader, for example Tecan Ultra (Tecan, Mannedorf, Switzerland).

One test compound is tested on the same microtitre plate in 10 different concentrations from 30 μM to 1 nM in duplicate determination. The data are normalized (enzyme reaction without inhibitor=0% inhibition, all assay components without enzyme=100% inhibition) and IC50 values are calculated using in-house software. Compounds in the context of the invention which were tested in this assay inhibited chymase activity with an IC50 of less than 10 μM.

IC50 values representative of the compounds of the invention are shown in Tables 1 and 2 below:

TABLE 1

| Example No. | Hamster chymase |
| --- | --- |
| 1 | 8 |
| 2 | 7 |
| 3 | 9 |
| 4 | 64 |
| 5 | 20 |
| 8 | 33 |
| 9 | 1500 |
| 10 | 1600 |
| 13 | 5 |
| 14 | 10 |
| 15 | 330 |
| 16 | 14 |
| 18 | 10 |
| 20 | 8 |
| 21 | 5 |
| 22 | 6 |
| 25 | 7 |
| 27 | 5 |
| 28 | 4 |
| 33 | 4 |
| 34 | 7 |
| 35 | 6 |
| 37 | 700 |
| 40 | 15 |
| 41 | 23 |
| 42 | 7 |
| 43 | 643 |
| 44 | 18 |
| 45 | 50 |
| 47 | 35 |
| 48 | 17 |
| 49 | 17 |
| 50 | 31 |
| 51 | 120 |
| 52 | 16 |
| 53 | 30 |
| 55 | 39 |
| 56 | 67 |
| 62 | 44 |
| 63 | 37 |
| 64 | 19 |
| 65 | 19 |

TABLE 1-continued

| Example No. | Hamster chymase |
| --- | --- |
| 66 | 30 |
| 67 | 4 |
| 75 | 82 |
| 76 | 41 |
| 77 | 170 |
| 78 | 140 |
| 79 | 210 |
| 81 | 65 |
| 82 | |
| 83 | 220 |
| 86 | 140 |
| 89 | 84 |
| 94 | 62 |
| 95 | 100 |
| 96 | 80 |
| 97 | 33 |
| 99 | 64 |
| 101 | 24 |
| 103 | 27 |
| 104 | 2 |
| 105 | 64 |
| 106 | 56 |
| 107 | 29 |
| 108 | 76 |
| 109 | 24 |
| 110 | 150 |
| 111 | 20 |
| 112 | |
| 113 | 6 |
| 114 | 7 |
| 115 | 10 |
| 116 | 20 |
| 117 | 3 |
| 118 | 6 |
| 119 | 280 |
| 120 | 1025 |
| 121 | 3 |
| 122 | 2 |
| 123 | 4 |
| 124 | 7 |
| 125 | 6 |
| 126 | 10 |
| 127 | 34 |
| 128 | 7 |
| 129 | 450 |
| 130 | 350 |
| 131 | 4 |
| 132 | 2 |
| 133 | 465 |
| 134 | 2 |
| 135 | 4 |
| 136 | 2 |
| 137 | 4 |
| 138 | 4 |
| 139 | 2 |
| 140 | 1 |
| 141 | 2 |
| 142 | 1 |
| 143 | 2 |
| 144 | 2 |
| 145 | 2 |
| 146 | 1 |
| 147 | 2 |
| 148 | 4 |
| 149 | 2 |
| 150 | 5 |
| 151 | 2 |
| 152 | 19 |
| 153 | 4 |
| 154 | 4 |
| 155 | 5 |
| 156 | 12 |
| 157 | 6 |
| 158 | 10 |
| 159 | 92 |
| 160 | 32 |
| 161 | 53 |
| 162 | 58 |

TABLE 1-continued

| Example No. | Hamster chymase |
| --- | --- |
| 163 | 28 |
| 164 | 34 |
| 165 | 40 |
| 166 | 62 |
| 167 | 91 |
| 168 | 49 |
| 169 | 370 |
| 170 | 20 |
| 171 | 17 |
| 172 | 27 |
| 173 | 110 |
| 174 | 44 |
| 175 | 8 |
| 176 | 29 |
| 177 | 30 |
| 178 | 16 |
| 179 | 10 |
| 180 | 7 |
| 181 | 4 |
| 182 | 4 |
| 183 | 10 |
| 184 | 170 |
| 185 | 140 |
| 186 | 23 |
| 187 | 4 |
| 188 | 4 |
| 189 | 3 |
| 190 | 140 |
| 191 | 16 |
| 192 | 5 |
| 193 | 8 |
| 194 | 13 |
| 195 | 4 |
| 196 | 6 |
| 197 | 10 |
| 198 | 54 |
| 199 | 8 |
| 200 | 4 |
| 201 | 7 |
| 202 | 4 |
| 203 | 20 |
| 204 | 39 |
| 205 | 3 |
| 206 | 3 |
| 207 | 4 |
| 209 | 13 |
| 211 | 20 |
| 213 | 18 |
| 214 | 20 |
| 215 | 26 |
| 216 | 183 |
| 217 | 1 |
| 218 | 4 |
| 219 | 5 |
| 220 | 6 |
| 221 | 10 |
| 222 | 12 |
| 223 | 3 |
| 224 | 2 |
| 225 | 4 |
| 226 | 3 |
| 227 | 2 |
| 228 | 14 |
| 229 | 4 |
| 230 | 170 |
| 231 | 21 |
| 232 | 6 |
| 233 | 470 |
| 234 | 270 |
| 235 | 9 |
| 236 | 5 |
| 238 | 45 |
| 239 | 490 |
| 240 | 67 |
| 241 | 2 |
| 242 | 40 |
| 243 | 6 |
| 244 | 2 |
| 245 | 67 |
| 246 | 1 |
| 247 | 1 |
| 248 | 2 |
| 249 | 200 |
| 250 | 37 |
| 251 | 420 |
| 252 | 190 |
| 253 | 1500 |
| 254 | 84 |
| 255 | 500 |
| 256 | 170 |
| 257 | 540 |
| 258 | 190 |
| 259 | 430 |
| 260 | 130 |
| 261 | 110 |
| 262 | 2100 |
| 263 | 38 |
| 264 | 31 |
| 265 | 2 |
| 266 | 59 |
| 267 | 16 |
| 268 | 18 |

TABLE 2

| Example No. | Hamster chymase |
| --- | --- |
| 269 | 14 |
| 270 | 6 |
| 271 | 23 |
| 272 | 11 |
| 273 | 1100 |
| 274 | 2 |
| 275 | 2300 |
| 276 | 4 |
| 277 | 2 |
| 278 | 5 |
| 279 | 4 |
| 280 | 250 |
| 281 | 1 |
| 282 | 88 |
| 283 | 40 |
| 284 | 11 |
| 285 | 42 |
| 286 | 37 |
| 287 | 4500 |
| 288 | 14 |
| 289 | 970 |
| 290 | 8 |
| 291 | 4 |
| 292 | |
| 293 | 12 |
| 294 | 2 |
| 295 | 8 |
| 296 | 3 |
| 297 | |
| 298 | 6 |
| 299 | 120 |
| 300 | 2 |
| 301 | 33 |
| 302 | 19 |
| 303 | 9 |

Rectovaginal Hamster Endometriosis-Fibrosis Model

To investigate the effect of the test substances on fibrosis mediated by endometriosis or the adhesions produced thereby, female syrian hamsters (ca. 150 g) aged 3-4 months are used. The cycle of the animals is determined via a vaginal smear needle. Oestrus in the animals is defined by the flow of a pus-like secretion from the vagina. On the day after oestrus, the operation is carried out to induce rectovaginal endometriosis and generate the adhesions, fibroses and fistulae associated thereto. Rectovaginal endometriosis is induced in the animals as follows: one day after oestrus, the animals are anaesthetized with isoflurane and the abdominal wall is opened. Approximately ⅓ rd of the uterus is removed and, in the piece removed, the endometrium is separated from the myometrium. Punches with a diameter of 5 mm are taken from the endometrium and each of these is sutured with 3 stitches. Here, the peritoneum is sutured with the uterus in the rectovaginal pouch and between the bladder and uterus. Subsequently, the abdominal wall is closed off by placing a suture. Endometriosis is thus generated by the adhesions which form within 21 days.

Starting on the day of the OP, the animals are treated daily with the test substance over a period of 21 days. The test substance is administered orally once daily at 2 ml/kg with ethanol, solutol, water (v/v/v=1/4/5) as vehicle and dosages of 3 mg/kg and 10 mg/kg. Disease severity is determined after sectioning the animals on day 21, based on adhesions and fistula development, in which the following scoring system is applied:

0=no adhesion, bladder freely moveable, no connection with the lesion, no fibrosis and adhesion,
1=slight adhesion, bladder not freely moveable, uterus moves slightly due to connection via the lesion, bladder slightly fused with the lesion and/or low adhesion of the lesion with the surrounding tissue, adhesion very fine and transparent,
2=moderate adhesion, bladder not freely moveable, uterus moves due to connection via the lesion, approximately half of the bladder fused with the lesion and/or adhesion of the lesion with the surrounding tissue,
3=severe adhesion, bladder not freely moveable, uterus moves vigorously due to connection via the lesion, bladder largely fused with the lesion and/or severe adhesion of the lesion with the surrounding tissue.

FIG. 1 shows a significant reduction in the adhesions caused by fibrosis, which were caused by an induced endometriosis, by the test substance example compound 189.

Hamster Adhesion Model

To investigate the effect of the test substances on a postoperative fibrosis and/or postoperative adhesions and fistulae, female syrian hamsters (each ca. 150 g) aged 3-4 months are used. The cycle of the animals is determined via a vaginal smear needle. During oestrus, a pus-like secretion may flow out of the vagina. On the day of oestrus, the operation to generate adhesions is carried out. For this purpose, the animals are anaesthetized with isoflurane and the abdominal cavity is opened. Four ischaemic nodes are each placed laterally on the peritoneal wall by basal ligation of a fold at a diameter of ca. 5 mm in size using a 4-0 silk suture. The gap between the nodes is ca. 1 cm in each case. Subsequently, the abdominal cavity is closed off by placing a suture. Starting on the day of the OP, the animals are treated daily with the test substance for 7 days. The test substance is administered orally once daily at 2 ml/kg with ethanol, solutol, water (v/v/v=1/4/5) as vehicle and dosages of 1 mg/kg, 3 mg/kg and 10 mg/kg. On day 7, the animals are sacrificed by decapitation or under deep isoflurane anaesthesia and autopsy is subsequently carried out. The number of adhesions per ischaemic node is determined and also their size and condition before the tissue is taken for histological and molecular biological analysis. In addition, tissue is preserved from the surrounding peritoneum as control tissue. Disease severity is determined after sectioning based on adhesions and fistula development. The scoring is undertaken for each ischaemic node individually, in which the following scoring system is applied:

0=no adhesion is found at the ischaemic nodes,
1=one adhesion with a blood vessel is found at the nodes,
2=more than one adhesion is found at the nodes,
3=many adhesions are found at the nodes, but this is just visible.

The average of the scores of all nodes per animal is then determined.

The invention claimed is:

1. A method for the treatment and/or prophylaxis of endometriosis, endometriosis-associated fibrosis, adenomyosis, and pain associated with an endometriosis disorder comprising administering to a patient in need thereof a therapeutically effective amount of a compound of the formula (I)

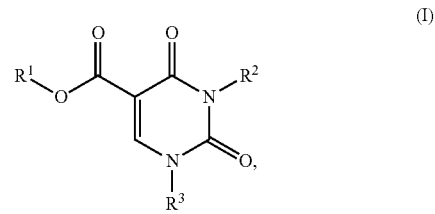

in which
$R^1$ is hydrogen or $(C_1\text{-}C_4)$-alkyl,
$R^2$ is a group of the formula

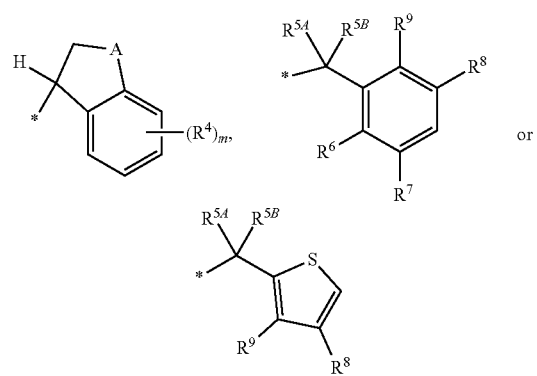

where
* is the point of attachment to the uracil nitrogen atom,
A is —CH$_2$—, —CH$_2$—CH$_2$—, —O—CH$_2$-## or oxygen,
    in which
    ## is the point of attachment to the phenyl ring,
m is a number 0, 1 or 2,
$R^4$ is halogen, difluoromethyl, trifluoromethyl, $(C_1\text{-}C_4)$-alkyl, difluoromethoxy, trifluoromethoxy or $(C_1\text{-}C_4)$-alkoxy,
$R^{5A}$ is hydrogen or deuterium,
$R^{5B}$ is hydrogen, deuterium or $(C_1\text{-}C_4)$-alkyl,
$R^6$ is hydrogen or fluorine,
$R^7$ is hydrogen or fluorine,
$R^8$ is halogen, difluoromethyl, trifluoromethyl, $(C_1\text{-}C_4)$-alkyl or nitro,
$R^9$ is hydrogen, halogen, difluoromethyl, trifluoromethyl, $(C_1\text{-}C_4)$-alkyl, nitro or $(C_1\text{-}C_4)$-alkylthio, $R^3$ is a group of the formula

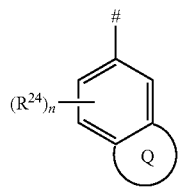

where
# is the point of attachment to the uracil nitrogen atom,
the ring Q is 5- to 7-membered heterocyclyl or 5- or 6-membered heteroaryl,
in which 5- to 7-membered heterocyclyl and 5- or 6-membered heteroaryl may be substituted by 1 to 4 substituents independently selected from the group of halogen, difluoromethyl, trifluoromethyl, trideuteromethyl, $(C_1-C_6)$-alkyl, $(C_3-C_7)$-cycloalkyl, oxo, hydroxyl, $(C_1-C_4)$-alkylcarbonyl, $(C_1-C_4)$-alkoxycarbonyl, aminocarbonyl and $(C_1-C_4)$-alkyl sulfonyl,
in which $(C_1-C_6)$-alkyl and $(C_3-C_7)$-cycloalkyl may in turn be substituted by 1 to 3 substituents independently selected from the group of halogen, cyano, trifluoromethyl, $(C_3-C_7)$-cycloalkyl, hydroxyl, $(C_1-C_4)$-alkoxy and 4- to 7-membered heterocyclyl,
and
in which two $(C_1-C_6)$-alkyl radicals bonded to a carbon atom of 5- to 7-membered heterocyclyl and 5- or 6-membered heteroaryl, together with the carbon atom to which they are bonded, may form a 3- to 6-membered carbocycle,
$R^{24}$ is halogen, $(C_1-C_4)$-alkyl or $(C_1-C_4)$-alkoxy,
n is a number 0, 1, 2 or 3,
or a salt, solvate or solvate of a salt thereof.

2. The method according to claim 1, in which
$R^1$ is hydrogen, methyl or ethyl,
$R^2$ is a group of the formula

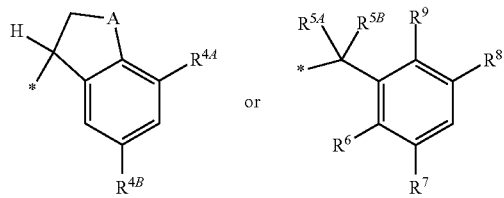

where
* is the point of attachment to the uracil nitrogen atom,
A is $CH_2$—, $-CH_2-CH_2-$, $-O-CH_2$-## or oxygen,
in which
## is the point of attachment to the phenyl ring,
$R^{4A}$ is hydrogen, fluorine, chlorine, trifluoromethyl or methyl,
$R^{4B}$ is hydrogen, fluorine, chlorine, trifluoromethyl or methyl,
with the proviso that at least one of the $R^{4A}$ and $R^{4B}$ radicals is not hydrogen,
$R^{5A}$ is hydrogen,
$R^{5B}$ is hydrogen,
$R^6$ is hydrogen,
$R^7$ is hydrogen,
$R^8$ is fluorine, chlorine, difluoromethyl, trifluoromethyl or methyl,
$R^9$ is fluorine, chlorine, difluoromethyl, trifluoromethyl or methyl,
$R^3$ is a group of the formula

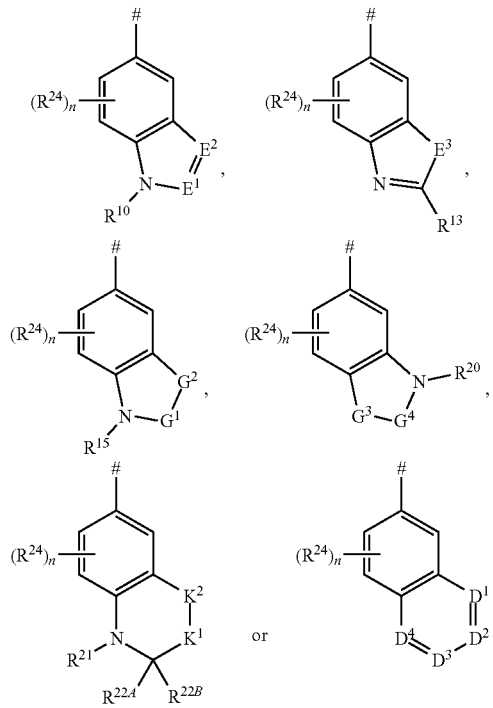

where
# is the point of attachment to the uracil nitrogen atom,
$E^1$ is $CR^{11}$ or N,
in which
$R^{11}$ is hydrogen, $(C_1-C_4)$-alkyl, $(C_3-C_7)$-cycloalkyl or aminocarbonyl,
$E^2$ is $CR^{12}$ or N,
in which
$R^{12}$ is hydrogen, $(C_1-C_4)$-alkyl or $(C_3-C_7)$-cycloalkyl,
$E^3$ is $NR^{14}$ or S,
in which
$R^{14}$ is hydrogen, $(C_1-C_4)$-alkyl or $(C_3-C_7)$-cycloalkyl,
$G^1$ is C=O or $SO_2$,
$G^2$ is $CR^{16A}R^{16B}$, $NR^{17}$, O or S,
in which
$R^{16A}$ is hydrogen, fluorine, $(C_1-C_4)$-alkyl or hydroxy,
$R^{16B}$ is hydrogen, fluorine, chlorine, $(C_1-C_4)$-alkyl or trifluoromethyl,
or
$R^{16A}$ and $R^{16B}$ together with the carbon atom to which they are bonded form a 3- to 6-membered carbocycle,
$R^{17}$ is hydrogen, $(C_1-C_6)$-alkyl, $(C_3-C_7)$-cycloalkyl or $(C_1-C_4)$-alkoxycarbonyl,
in which $(C_1-C_6)$-alkyl may be substituted by 1 to 3 substituents independently selected from the group of fluorine, trifluoromethyl, cyano, $(C_3-C_7)$-cycloalkyl, hydroxyl, trifluoromethoxy, (C$_1$-C$_4$)-alkoxy, azetidinyl, oxetanyl, tetrahydrofuranyl and pyrrolidinyl, G$^3$ is CR$^{18A}$R$^{18B}$, NR$^{19}$, O or S, in which R$^{18A}$ is hydrogen, fluorine, (C$_1$-C$_4$)-alkyl or hydroxy, R$^{18B}$ is hydrogen, fluorine, chlorine, (C$_1$-C$_4$)-alkyl or trifluoromethyl, or R$^{18A}$ and R$^{18B}$ together with the carbon atom to which they are bonded form a 3- to 6-membered carbocycle, R$^{19}$ is hydrogen, (C$_1$-C$_6$)-alkyl, (C$_3$-C$_7$)-cycloalkyl or (C$_1$-C$_4$)-alkoxycarbonyl, in which (C$_1$-C$_6$)-alkyl may be substituted by 1 to 3 substituents independently selected from the group of fluorine, trifluoromethyl, cyano, (C$_3$-C$_7$)-cycloalkyl, hydroxyl, trifluoromethoxy, (C$_1$-C$_4$)-alkoxy, azetidinyl, oxetanyl, tetrahydrofuranyl and pyrrolidinyl, G$^4$ is CH$_2$, C=O or SO$_2$, K$^1$ is CH$_2$ or O, K$^2$ is CH$_2$ or O, with the proviso that only one of the K$^1$ and K$^2$ groups is O, D$^1$, D$^2$, D$^3$ and D$^4$ are each independently CR$^{23}$ or N, in which R$^{23}$ is hydrogen, halogen, (C$_1$-C$_6$)-alkyl or (C$_3$-C$_7$)-cycloalkyl, with the proviso that not more than 2 of the D$^1$, D$^2$, D$^3$ and D$^4$ groups are N, R$^{24}$ is fluorine or methyl, n is a number 0 or 1, R$^{10}$ is (C$_1$-C$_4$)-alkyl or (C$_3$-C$_7$)-cycloalkyl, in which (C$_1$-C$_4$)-alkyl may be substituted by 1 or 2 substituents independently selected from the group of fluorine, trifluoromethyl, cyclopropyl, cyclobutyl, hydroxyl, methoxy, ethoxy, azetidinyl, oxetanyl, tetrahydrofuranyl and pyrrolidinyl, R$^3$ is hydrogen, (C$_1$-C$_4$)-alkyl or (C$_3$-C$_7$)-cycloalkyl, R$^{15}$ is hydrogen, (C$_1$-C$_6$)-alkyl or (C$_3$-C$_7$)-cycloalkyl, in which (C$_1$-C$_6$)-alkyl may be substituted by 1 or 2 substituents independently selected from the group of fluorine, trifluoromethyl, cyclopropyl, cyclobutyl, hydroxyl, methoxy, ethoxy, azetidinyl, oxetanyl, tetrahydrofuranyl and pyrrolidinyl, R$^{20}$ is hydrogen, (C$_1$-C$_6$)-alkyl, (C$_3$-C$_7$)-cycloalkyl or (C$_1$-C$_4$)-alkylcarbonyl, in which (C$_1$-C$_6$)-alkyl may be substituted by 1 or 2 substituents independently selected from the group of fluorine, trifluoromethyl, cyclopropyl, cyclobutyl, hydroxyl, methoxy, ethoxy, azetidinyl, oxetanyl, tetrahydrofuranyl and pyrrolidinyl, R$^{21}$ is hydrogen, (C$_1$-C$_6$)-alkyl, (C$_3$-C$_7$)-cycloalkyl or (C$_1$-C$_4$)-alkylsulfonyl, R$^{22A}$ is hydrogen or C$_1$-C$_4$-alkyl, R$^{22B}$ is hydrogen or C$_1$-C$_4$-alkyl, or R$^{22A}$ and R$^{22B}$ together with the carbon atom to which they are bonded form a carbonyl group.

3. The method according to claim 1, in which

R$^1$ is hydrogen,

R$^2$ is a group of the formula

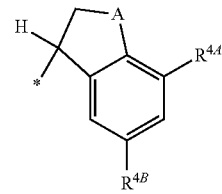

where

* is the point of attachment to the uracil nitrogen atom,

A is —CH$_2$—,

R$^{4A}$ is chlorine or trifluoromethyl,

R$^{4B}$ is hydrogen,

R$^3$ is a group of the formula

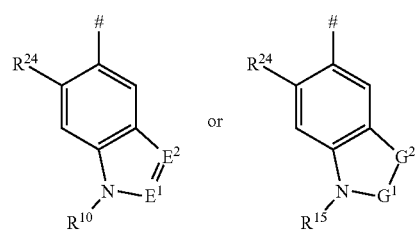

where # is the point of attachment to the uracil nitrogen atom,

E$^1$ is CR$^{11}$, in which

R$^{11}$ is hydrogen,

E$^2$ is N,

G$^1$ is C=O,

G$^2$ is CR$^{16A}$R$^{16B}$, NR$^{17}$, O or S, in which

R$^{16A}$ is hydrogen, fluorine, methyl or hydroxy,

R$^{16B}$ is hydrogen, fluorine, methyl or trifluoromethyl, or

R$^{16A}$ and R$^{16B}$ together with the carbon atom to which they are bonded form a cyclopropyl ring, R$^{17}$ is hydrogen, (C$_1$-C$_4$)-alkyl or (C$_3$-C$_5$)-cycloalkyl, in which (C$_1$-C$_4$)-alkyl may be substituted by 1 to 3 substituents independently selected from the group of fluorine, trifluoromethyl, cyano, cyclopropyl, cyclobutyl, hydroxyl, trifluoromethoxy, methoxy, ethoxy, azetidinyl, oxetanyl, tetrahydrofuranyl and pyrrolidinyl, R$^{24}$ is hydrogen or fluorine, R$^{10}$ is (C$_1$-C$_4$)-alkyl, and R$^{15}$ is hydrogen, methyl or ethyl, in which methyl and ethyl may be substituted by 1 substituent selected from the group of fluorine, trifluoromethyl and cyclopropyl.

4. The method according to claim 1, in which
$R^1$ is hydrogen,
$R^2$ is a group of the formula

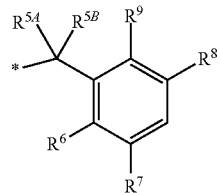

where
* is the point of attachment to the uracil nitrogen atom,
$R^{5A}$ is hydrogen,
$R^{5B}$ is hydrogen,
$R^6$ is hydrogen,
$R^7$ is hydrogen,
$R^8$ is fluorine, chlorine or trifluoromethyl,
$R^9$ is fluorine, chlorine, trifluoromethyl or methyl,
$R^3$ is a group of the formula

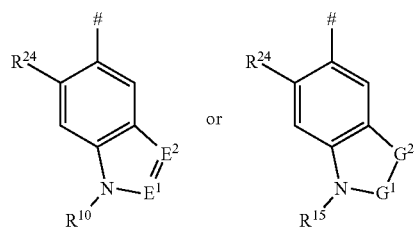

where
# is the point of attachment to the uracil nitrogen atom,
$E^1$ is $CR^{11}$,
  in which
    $R^{11}$ is hydrogen,
$E^2$ is N,
$G^1$ is C=O,
$G^2$ is $CR^{16A}R^{16B}$, $NR^{17}$, O or S,
  in which
    $R^{16A}$ is hydrogen, fluorine, methyl or hydroxy,
    $R^{16B}$ is hydrogen, fluorine, methyl or trifluoromethyl,
    or
    $R^{16A}$ and $R^{16B}$ together with the carbon atom to which they are bonded form a cyclopropyl ring,
    $R^{17}$ is hydrogen, $(C_1-C_4)$-alkyl or $(C_3-C_5)$-cycloalkyl,
      in which $(C_1-C_4)$-alkyl may be substituted by 1 to 3 substituents independently selected from the group of fluorine, trifluoromethyl, cyano, cyclopropyl, cyclobutyl, hydroxyl, trifluoromethoxy, methoxy, ethoxy, azetidinyl, oxetanyl, tetrahydrofuranyl and pyrrolidinyl,
$R^{24}$ is hydrogen or fluorine,
$R^{10}$ is $(C_1-C_4)$-alkyl, and
$R^{15}$ is hydrogen, methyl or ethyl,
  in which methyl and ethyl may be substituted by 1 substituent selected from the group of fluorine, trifluoromethyl and cyclopropyl.

5. A method for the treatment and/or prophylaxis of chronic pain in the pelvic cavity which is not associated with endometriosis comprising administering to a patient in need thereof a therapeutically effective amount of the compound of formula (I)

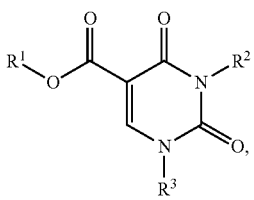

in which
$R^1$ is hydrogen or $(C_1-C_4)$-alkyl,
$R^2$ is a group of the formula

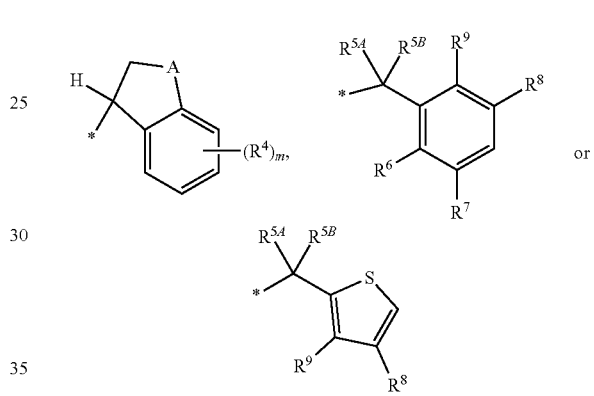

where
* is the point of attachment to the uracil nitrogen atom,
A is —$CH_2$—, —$CH_2$—$CH_2$—, —O—$CH_2$-## or oxygen,
  in which
    ## is the point of attachment to the phenyl ring,
m is a number 0, 1 or 2,
$R^4$ is halogen, difluoromethyl, trifluoromethyl, $(C_1-C_4)$-alkyl, difluoromethoxy, trifluoromethoxy or $(C_1-C_4)$-alkoxy,
$R^{5A}$ is hydrogen or deuterium,
$R^{5B}$ is hydrogen, deuterium or $(C_1-C_4)$-alkyl,
$R^6$ is hydrogen or fluorine,
$R^7$ is hydrogen or fluorine,
$R^8$ is halogen, difluoromethyl, trifluoromethyl, $(C_1-C_4)$-alkyl or nitro,
$R^9$ is hydrogen, halogen, difluoromethyl, trifluoromethyl, $(C_1-C_4)$-alkyl, nitro or $(C_1-C_4)$-alkylthio,
$R^3$ is a group of the formula

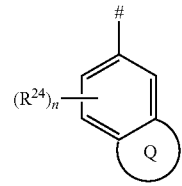

where
# is the point of attachment to the uracil nitrogen atom,
the ring Q is 5- to 7-membered heterocyclyl or 5- or 6-membered heteroaryl,
- in which 5- to 7-membered heterocyclyl and 5- or 6-membered heteroaryl may be substituted by 1 to 4 substituents independently selected from the group of halogen, difluoromethyl, trifluoromethyl, trideuteromethyl, $(C_1-C_6)$-alkyl, $(C_3-C_7)$-cycloalkyl, oxo, hydroxyl, $(C_1-C_4)$-alkylcarbonyl, $(C_1-C_4)$-alkoxycarbonyl, aminocarbonyl and $(C_1-C_4)$-alkyl sulfonyl,
  - in which $(C_1-C_6)$-alkyl and $(C_3-C_7)$-cycloalkyl may in turn be substituted by 1 to 3 substituents independently selected from the group of halogen, cyano, trifluoromethyl, $(C_3-C_7)$-cycloalkyl, hydroxyl, $(C_1-C_4)$-alkoxy and 4- to 7-membered heterocyclyl,
  - and
  - in which two $(C_1-C_6)$-alkyl radicals bonded to a carbon atom of 5- to 7-membered heterocyclyl and 5- or 6-membered heteroaryl, together with the carbon atom to which they are bonded, may form a 3- to 6-membered carbocycle, $R^{24}$ is halogen, $(C_1-C_4)$-alkyl or $(C_1-C_4)$-alkoxy,
n is a number 0, 1, 2 or 3,
or a salt solvate or solvate of a salt thereof.

* * * * *